US008071734B2

(12) United States Patent
Stanton et al.

(10) Patent No.: US 8,071,734 B2
(45) Date of Patent: *Dec. 6, 2011

(54) NUCLEIC ACID-BASED DETECTION

(75) Inventors: Martin Stanton, Stow, MA (US); Pieter Wensink, Wellesley, MA (US); Alexander Stewart, Waltham, MA (US)

(73) Assignee: Brandeis University, Waltham, MA (US)

( * ) Notice: Subject to any disclaimer, the term of this patent is extended or adjusted under 35 U.S.C. 154(b) by 1035 days.

This patent is subject to a terminal disclaimer.

(21) Appl. No.: 11/645,362

(22) Filed: Dec. 22, 2006

(65) Prior Publication Data
US 2008/0020939 A1 Jan. 24, 2008

Related U.S. Application Data

(63) Continuation of application No. 10/668,507, filed on Sep. 23, 2003, now abandoned, which is a continuation of application No. 09/569,960, filed on May 12, 2000, now Pat. No. 6,680,377.

(60) Provisional application No. 60/174,398, filed on Jan. 5, 2000, provisional application No. 60/134,330, filed on May 14, 1999.

(51) Int. Cl.
*C07H 21/04* (2006.01)

(52) U.S. Cl. .......... 536/22.1; 536/23.1; 436/501; 435/6; 435/18; 435/19

(58) Field of Classification Search .................. None
See application file for complete search history.

(56) References Cited

U.S. PATENT DOCUMENTS

| 4,781,458 | A |   | 11/1988 | Angel et al.     | 356/301  |
| 5,118,801 | A |   | 6/1992  | Lizardi et al.   | 536/27   |
| 5,270,163 | A |   | 12/1993 | Gold et al.      | 435/6    |
| 5,485,277 | A |   | 1/1996  | Foster           | 356/445  |
| 5,567,588 | A |   | 10/1996 | Gold et al.      | 435/6    |
| 5,593,835 | A |   | 1/1997  | Rando et al.     | 435/6    |
| 5,674,688 | A |   | 10/1997 | Kauvar et al.    |          |
| 5,691,145 | A |   | 11/1997 | Pitner et al.    | 435/6    |
| 5,771,097 | A |   | 6/1998  | Kusunose et al.  | 356/353  |
| 5,837,466 | A |   | 11/1998 | Lane et al.      | 435/6    |
| 5,843,653 | A |   | 12/1998 | Gold et al.      | 435/6    |
| 5,874,219 | A |   | 2/1999  | Rava et al.      |          |
| 5,989,823 | A |   | 11/1999 | Jayasena et al.  | 435/6    |
| 6,037,130 | A |   | 3/2000  | Tyagi et al.     | 435/6    |
| 6,103,476 | A |   | 8/2000  | Tyagi et al.     | 435/6    |
| 6,147,204 | A | * | 11/2000 | Gold et al.      | 536/24.5 |
| 6,150,097 | A |   | 11/2000 | Tyagi et al.     | 435/6    |

FOREIGN PATENT DOCUMENTS

| EP | 0826780     | 3/1998 |
| JP | 10-293128 A | 11/1998 |
| WO | WO97/38134  | 10/1997 |
| WO | WO 97/42345 | 11/1997 |
| WO | WO 97/49989 | 12/1997 |
| WO | WO98/10096  | 3/1998 |
| WO | WO/99/05314 | 2/1999 |
| WO | WO99/31275  | 6/1999 |
| WO | WO00/06778  | 2/2000 |

OTHER PUBLICATIONS

Bacher et al., "Nucleic Acid Selection as a Tool for Drug Discovery," *Drug Discovery Today*, 3(6):265-273 (1998).
Cardullo et al., "Detection of nucleic acid hybridization by nonradiative fluorescence resonance energy transfer,"*Proc. Natl. Acad. Sci. USA*, 8:8790-8794 (Dec. 1988).
Ciesiolka et al., "Affinity Selection-Amplification from Randomized Ribooligonucleotide Pools," *Methods in Enzymology*, 267:315-35 (1996).
Conrad et al., "Detecting Immobilized Protein Kinase C Isozymes with RNA Aptamers," *Analytical Biochemistry*, Article No. 0462, 242:261-265 (1996).
Conrad et al., "In Vitro Selection of Nucleic Acid Aptamers That Bind Proteins," *Methods in Enzymology*, 267:336-383 (1996).
Davis et al., "Staining of cell surface human CD4 with 2'-F-pyrimidine-containing RNA aptamers for flow cytometry," *Nucleic Acids Research*, 26(17):3915-3924 (1998).
Ellington et al., "In vitro selection of RNA molecules that bind specific ligands," *Nature*, 346:818-822 (1990).
Fang et al., "Designing a Novel Molecular Beacon for Surface-Immobilized DNA Hybridization Studies", *Journal of the Am. Chem Society*, 121(12):2921-2922 (1999).
Feigon et al., "Aptamer Structures From A to Zeta", *Chemistry & Biology*, 3(8):611-617 (1996).
Fitzwater et al., "A SELEX Primer," *Methods in Enzymology*, 267:275-301 (1996).
Gold et al., "Diversity of Oligonucleotide Functions," *Annu. Rev. Biochem.*, 64:763-97 (1995).
Gold, "Oligonucleotides as Research, Diagnostic, and Therapeutic Agents," *The American Society for Biochemistry and Molecular Biology, Inc.*, 270(23):13581-13584 (1995).
Griffiths et al., *The EMBO Journal*, 13:3245-3260 (1994).
Hamaguchi et al., "Aptamer Beacons for the Direct Detection of Proteins", *Analytical Biochemistry*, 294(2):126-131 (2001).
Jayasena, "Aptamers: An Emerging Class of Molecules That Rival Antibodies in Diagnostics." *Clin. Chem.*, 45(9):1628-50 (1999).

(Continued)

*Primary Examiner* — Kimberly Chong
(74) *Attorney, Agent, or Firm* — Swanson & Bratschun, L.L.C.

(57) ABSTRACT

The invention relates to compositions, systems, and methods for simultaneously detecting the presence and quantity of one or more different compounds in a sample using aptamer beacons. Aptamer beacons are oligonucleotides that have a binding region that can bind to a non-nucleotide target molecule, such as a protein, a steroid, or an inorganic molecule. New aptamer beacons having binding regions configured to bind to different target molecules can be used in solution-based and solid, array-based systems. The aptamer beacons can be attached to solid supports, e.g., at different predetermined points in two-dimensional arrays. The invention includes devices, methods, and computer software for carrying out the methods.

39 Claims, 16 Drawing Sheets

OTHER PUBLICATIONS

Kramer, "Molecular Beacons: Hybridization Probes for Detection of Nucleic Acids in Homogenous Solutions," http://www.molecularbeacons.com (Dec. 7, 1998).

Lashkari et al., "Yeast Microarrays for Genome Wide Parallel Genetic and Gene Expression Analysis," *Proc. Nat'l Acad. Sci. USA*, 94:13057-62 (1997).

Lin et al., "Modified RNA sequence pools for in vitro selection," *Nucleic Acids Research*, 22(24):5229-5234 (1994).

Morgan et al., "A surface plasmon resonance immunosensor based on the streptavidin-biotin complex," *Biosensors & Bioelectronics*, 7:405-410 (1992).

Morris et al., "High affinity ligands from in vitro selection: complex targets." *Proc. Natl. Acad. Sci.*, USA, 95(6):2902-7 (1998).

Osborne et al., "Aptamers as therapeutic and diagnostic reagents: problems and prospects," *Chemical Biology*, 1:5-9 (1997).

Pagratis et al., "Potent 2'-amino-, and 2'-fluoro-2'-deoxyribonucleotide RNA inhibitors of keratinocyte growth factor," *Nature Biotechnology*, 15:68-73 (1997).

Patel et al., "Structure, Recognition and Adaptive Binding in RNA Aptamer Complexes", *Jour. Of Molecular Biology*, 272(5):645-664 (1997).

Pease et al., "Light Generated Oligonucleotide Arrays for Rapid DNA Sequence Analysis," *Proc. Nat'l Acad. Sci. USA*, 91:5022-26 (1994).

Potyrailo et al., "Adapting Selected Nucleic Acid Ligands (Aptamers) to Biosensors," *Anal. Chem.*, 70:3419-3425 (1998).

Shalon et al., "A DNA Microarray System for Analyzing Complex DNA Samples Using Two-Color Fluorescent Probe Hybridization," *Genome Res.*, 6:639-45 (1996).

Schena et al., "Parallel Human Genome Analysis: Microarray-Based Expression Monitoring of 1000 Genes," *Proc. Nat'l Acad. Sci. USA*, 93: 10514-19 (1996).

Sixou et al., "Intracellular Oligonucleotide Hybridization Detected by Fluorescence Resonance Energy Transfer (FRET)," *Nucleic Acids Res.*, 22:662-68 (1994).

Tasset et al., "Oligonucleotide Inhibitors of Human Thrombin that Bind Distinct Epitopes", *Journal of Molecular Biology*, 272(5):688-698 (1997).

Tyagi et al., "Molecular Beacons: Probes That Fluoresce Upon Hybridization," *Nature Biotech.*, 14:303-08 (1996).

\* cited by examiner

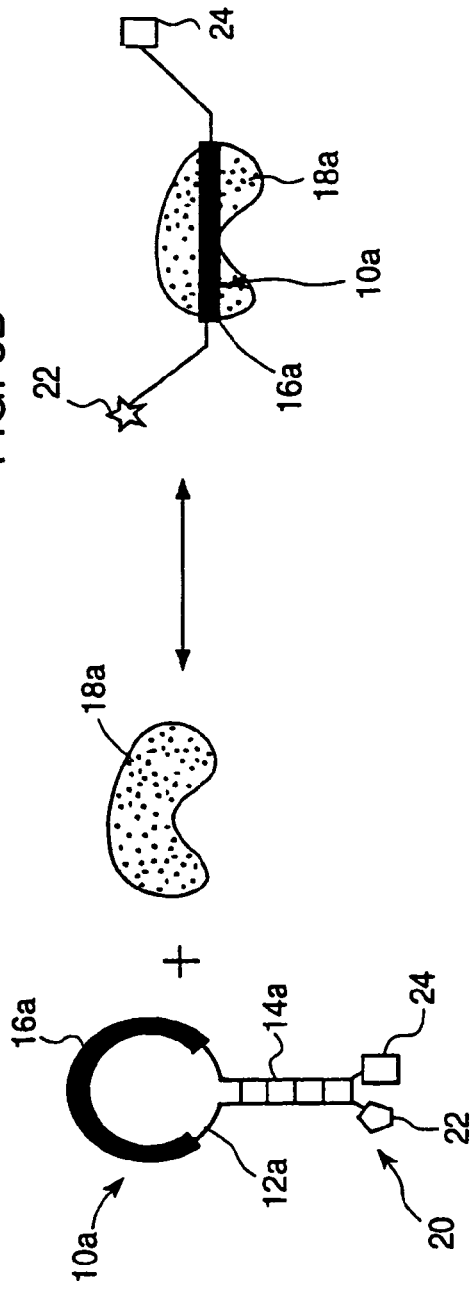
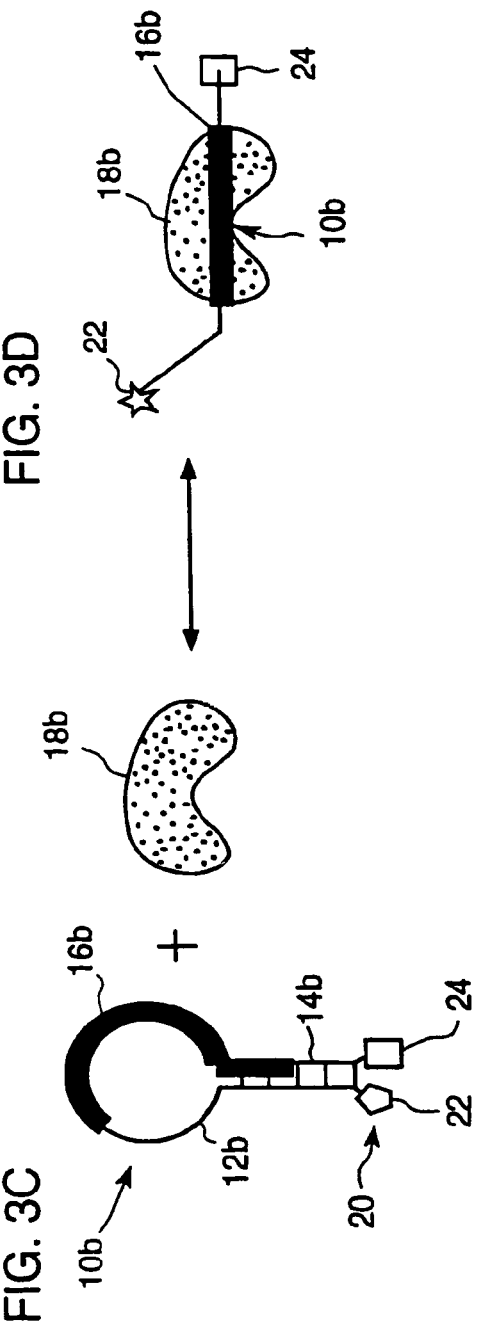

FIG. 12
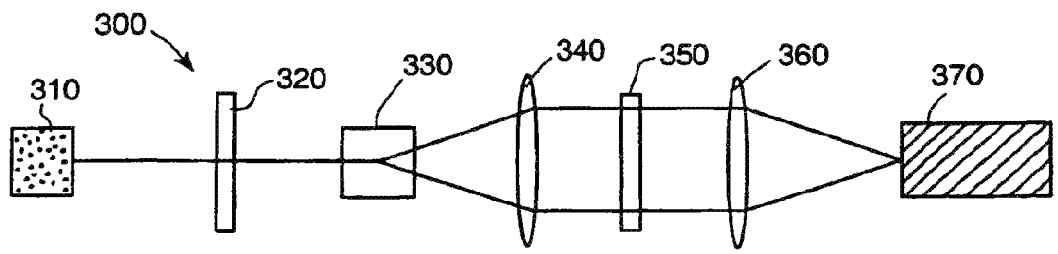
| FIG. 13A | FIG. 13B | FIG. 13C | FIG. 13D |
|---|---|---|---|
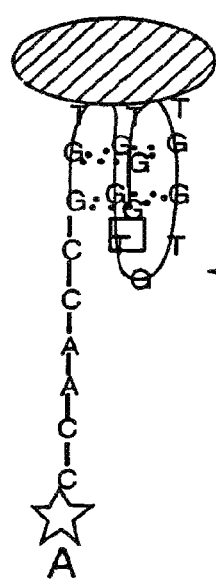 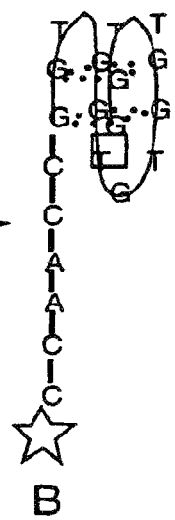  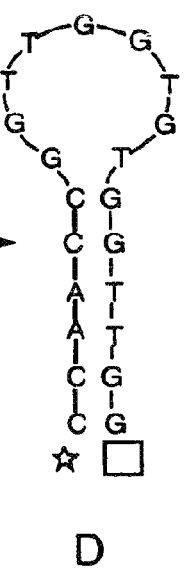
| A | B | C | D |
|---|---|---|---|
| SEQ ID NO: 4 | SEQ ID NO: 4 | SEQ ID NO: 4 | SEQ ID NO: 4 |

SEQUENCE LISTING

<160> NUMBER OF SEQ ID NOS: 7

<210> SEQ ID NO 1
<211> LENGTH: 15
<212> TYPE: DNA
<213> ORGANISM: Artificial Sequence
<220> FEATURE:
<223> OTHER INFORMATION: Synthetically generated oligonucleotide

<400> SEQUENCE: 1
ggttggtgtg gttgg                                                    15

<210> SEQ ID NO 2
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 2
ccaaggttgg tgtggttgg                                                19

<210> SEQ ID NO 3
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 3
ccaacggttg gtgtggttgg                                               20

<210> SEQ ID NO 4
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 4
ccaaccggtt ggtgtggttg g                                             21

<210> SEQ ID NO 5
<211> LENGTH: 22

-continued

```
<212> TYPE: DNA
<213> ORGANISM: Artificial Sequence
<220> FEATURE:
<223> OTHER INFORMATION: Synthetically generated oligonucleotide

<400> SEQUENCE: 5
ccaaccaggt tggtgtggtt gg                                           22

<210> SEQ ID NO 6
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 6
tttttggttg gtgtggttgg                                              20

<210> SEQ ID NO 7
<211> LENGTH: 18
<212> TYPE: DNA
<213> ORGANISM: Artificial Sequence
<220> FEATURE:
<223> OTHER INFORMATION: Synthetically generated oligonucleotide

<400> SEQUENCE: 7
ccaaccacac caagttgg                                                18
```

US 8,071,734 B2

NUCLEIC ACID-BASED DETECTION

CROSS REFERENCE TO RELATED APPLICATIONS

This application is a continuation of U.S. application Ser. No. 10/668,507, filed on Sep. 23, 2003 now abandoned, which is a continuation of prior U.S. application Ser. No. 09/569,960, filed on May 12, 2000 now U.S. Pat. No. 6,680,377, which claims the benefit of prior U.S. provisional application No. 60/174,398, filed on Jan. 5, 2000, and prior U.S. provisional application No. 60/134,330, filed on May 14, 1999. The entire contents of each of these four prior applications are incorporated herein by reference.

FIELD OF THE INVENTION

The invention relates to compositions, systems, and methods for detecting molecular species using nucleic acids.

BACKGROUND OF THE INVENTION

Various types of systems have been used to detect the presence of a particular chemical or molecule in a complex sample. For example, antibodies are used to detect the presence of a protein in a sample, and DNA microarray chips have been used to identify genes and study gene expression. Most existing molecular detection systems are designed to detect the presence of a single type or single category of target molecule. In the case of antibody detection, existing systems are typically limited to detecting only a subset of a type of molecule.

Recently, it has been shown that RNA and DNA aptamers can substitute for monoclonal antibodies in various applications (Jayasena, "Aptamers: an emerging class of molecules that rival antibodies in diagnostics." Clin. Chem., 45(9):1628-50, 1999; Morris et al., "High affinity ligands from in vitro selection: complex targets." Proc. Natl. Acad. Sci., USA, 95(6):2902-7, 1998). The relatively fast selection process of the specific aptamers and the inexpensive synthesis makes the aptamer useful alternatives for monoclonal antibodies. These nucleic acids can be easily synthesized, readily manipulated, and can be stored for over long time. These benefits make nucleic acids more attractive biotechnology tools than their counterpart of proteins, antibodies. Additionally these nucleic acid probes can also be labeled by radioisotope, biotin, or fluorescent tags and can be used to detect targets under various conditions. An increasing number of DNA and RNA aptamers that recognize their non-nucleic acid targets has been developed by SELEX and has been characterized (Gold et al., "Diversity of Oligonucleotide Functions," Annu. Rev. Biochem., 64:763-97.1995; Bacher & Ellington, "Nucleic Acid Selection as a Tool for Drug Discovery," Drug Discovery Today, 3(6):265-273, 1998).

SUMMARY OF THE INVENTION

The invention relates to new compositions, systems, and methods for simultaneously detecting the presence and quantity of one or more different compounds in a sample using novel nucleic acid sensor molecules. Nucleic acids have previously been shown to be capable of specifically binding with high affinity to non-nucleotide target molecules, such as proteins, small organic molecules, or inorganic molecules. These nucleic acids are commonly referred to as aptamers. An aptamer can be either an RNA or a DNA composed of naturally occurring or modified nucleotides.

In the new compositions, standard aptamers are bioengineered such that binding of a bioengineered aptamer to a target molecule causes a change in the conformation of the bioengineered aptamer. Furthermore, one or more reporter moieties or groups are included in the bioengineered aptamers such that the change in bioengineered aptamer conformation results in a detectable change of a physical property of the reporter group (or the engineered aptamer itself). These bioengineered aptamers are referred to herein as aptamer beacons.

Aptamer beacons having binding regions configured to bind to different target molecules can be used in various detection methods and systems. For example the new aptamer beacons can be used in solution-based assays, or can be attached to a solid support, e.g., at different predetermined points in a one or two-dimensional array, for use in solid-based assays. The aptamer beacons or aptamer beacon arrays are then exposed to the sample, such that target molecules in the sample bind to their respective aptamer beacons. The presence of bound target molecules can be detected by measuring a change in a physical property of the aptamer beacon reporter group, e.g., by observing a change in fluorescence efficiency of the aptamer beacon.

To assist in analyzing the sample, the new detection systems can include pattern recognition software. The software compares the target molecule binding pattern corresponding to the unknown sample with binding patterns corresponding to known compounds. From these comparisons, the software can determine the composition of the sample, or deduce information about the source of the sample.

The systems can be used to detect the existence of characteristic compounds, or "molecular fingerprints," associated with certain chemicals or conditions. For example, the systems can be used for human drug testing by detecting the presence of metabolites of particular drugs. The systems can also be used to infer the existence of a disease (e.g., cancer) by detecting the presence of compounds associated with the disease state, or for pollution monitoring by detecting compounds characteristic of the discharge of certain pollutants. Numerous other applications are also possible.

In general, the invention features an aptamer beacon that binds to a non-nucleic acid target molecule and that includes an oligonucleotide including a loop portion, a first segment, and a second segment complementary to the first segment, wherein the first and second segments form a stem portion when hybridized together; a binding region formed by the oligonucleotide and configured to bind to the non-nucleic acid target molecule; a first reporter moiety, e.g., a fluorophore, attached to the first segment; and a second reporter moiety, e.g., a chemical quencher, attached to the second segment, wherein the first and second reporter moieties interact to produce a detectable signal when the distance between them is changed; wherein binding of the target molecule to the binding region breaks base pair bonds in the stem portion, causing a change in conformation of the aptamer beacon that separates the first and second segments, thereby altering the distance between the first and second reporter moieties, and producing a detectable signal.

A conformational change in an aptamer beacon is an alteration in the secondary and/or tertiary structure of the oligonucleotide that makes up the aptamer beacon. A conformational change typically results in the addition and/or deletion of basepairing interactions in the between alternate forms of the aptamer beacon.

In these new aptamer beacons, when the first reporter moiety is a fluorophore and the second reporter moiety is a chemical quencher, the quencher quenches the fluorophore when the first and second segments are hybridized together to form the stem portion, and wherein binding of a target molecule to the binding region breaks base pair bonding in the stem portion, causing the first and second segments to separate and the fluorophore to separate from the chemical group, thereby ending the quenching and enabling the fluorophore to emit detectable fluorescence.

In these aptamer beacons, the binding region can be located entirely or partially within the loop portion, the stem portion, or at least partially in both. In addition, the first and second reporter moieties can be an enzyme and a corresponding ligand, and the first and second segments can include 4, 5, 6, or 7 nucleotides each.

The invention also features an aptamer beacon that binds to a non-nucleic acid target molecule and that includes an oligonucleotide including a first segment, a second segment, and a third segment located between the first and second segments, wherein the first and second segments form a complex, e.g., a hybrid duplex or other secondary or tertiary structure, when the aptamer beacon is not bound to the target molecule; a binding region formed by the aptamer beacon when contacting the target molecule; a first reporter moiety attached to the first segment; and a second reporter moiety attached to the second segment, wherein the first and second reporter moieties interact to produce a detectable signal when the distance between them is changed; wherein binding of the target molecule to the binding region breaks base pair bonds in the complex causing a change in conformation of the aptamer beacon that alters the distance between the first and second reporter moieties, and producing a detectable signal.

In these aptamer beacons, the first reporter moiety can be an energy absorbing moiety and the second reporter moiety can be a fluorescence emitting moiety, such that when the first and second reporter moieties are in sufficiently close proximity, the absorbing moiety allows an energy transfer between the moieties, thereby allowing the emitting moiety to emit fluoresce; and wherein binding of a target molecule to the binding region causes the first and second segments to hybridize together.

In another aspect, the invention features a device for simultaneously detecting the presence of a plurality of different, non-nucleic acid target molecules in a sample. The devices include: a solid support; and a plurality of different aptamer beacons bound to the support, each aptamer beacon having a first end attached to the support, and a binding region that binds to a specific non-nucleic acid target molecule, wherein the binding regions of different aptamer beacons bind to different target molecules. In these devices, the solid support can be a glass surface to which the first ends of the aptamer beacons are covalently bound. In addition, the solid support can be a planar surface, and the aptamer beacons can be distributed on the planar surface in a two-dimensional array. Spots of identical aptamer beacons can be located at different points in the two-dimensional array.

The binding region of at least one of the aptamer beacons in the device can be configured to bind to a non-nucleic acid target molecule selected from the group consisting of a protein, a steroid, and an inorganic molecule. The aptamer beacons can comprise RNA, DNA, modified RNA, modified RNA, or a combination thereof. In addition, each aptamer beacon can comprise a reporter group, such as a fluorophore, for signaling binding of a target molecule to the binding region.

The invention also features a method of detecting the presence or absence of one or more different target molecules in a sample, by obtaining a plurality of the new aptamer beacons; contacting the sample to the aptamer beacons, such that any target molecules in the sample can bind to corresponding binding regions of the aptamer beacons; and detecting the presence of target molecules bound to the aptamer beacons. The aptamer beacons can be in a liquid, or can be bound to a solid support, such as a particle or a plate. In some embodiments, the aptamer beacons emit fluorescent radiation when excited by evanescent waves.

In this method, different spots, each spot including a plurality of identical aptamer beacons, can be distributed on the solid support in a predetermined array, and the method can further include comparing a fluorescence pattern of the sample to known fluorescence patterns, e.g., with a computer program, disposed on a computer readable medium, that includes instructions for causing a processor to compare the fluorescence pattern of the sample to a library of known fluorescence patterns; and select the combination of known fluorescence patterns that most closely matches the fluorescence pattern of the sample.

The detecting step can also include detecting a change in the Raman emission frequencies of an aptamer beacon caused when a target molecule binds to the aptamer beacon.

In another aspect, the invention features a computer program, disposed on a computer-readable medium, for analyzing the output of an assay that determines the composition of a sample and deduces the presence or absence of known abnormal conditions, the computer program including instructions for causing a processor to: compare the assay output, e.g., an image, to a library of known outputs corresponding to subjecting samples of known composition to the assay; select a combination of known outputs that most closely matches the assay outputs; compare any deviation between the sample output and the combination of known outputs to a library of known deviations, the known deviations being caused by known abnormal conditions; and deduce the presence or absence of known abnormal conditions. For example, the known abnormal conditions can include the presence of abnormal compounds in the sample, and the presence of normal compounds in abnormal quantities.

The invention also features a method for analyzing the output of an assay that determines the composition of a sample and deduces the presence or absence of known abnormal conditions by comparing the assay output to a library of known outputs corresponding to subjecting samples of known composition to the assay; selecting a combination of known outputs that most closely matches the assay outputs; comparing any deviation between the sample output and the combination of known outputs to a library of known deviations, the known deviations being caused by known abnormal conditions; and deducing the presence or absence of known abnormal conditions.

In yet another aspect, the invention features a device for detecting the presence of a target molecule in a sample. The device includes a solid support; and a plurality of different aptamer beacons bound to the support, each aptamer beacon having a first end attached to the support, and a binding region that binds to a specific enantiomer of the target molecule, wherein the binding regions of different aptamer beacons bind to different enantiomers of the target molecule.

Furthermore, the invention includes a device for detecting the presence of a target in a sample. The device includes a solid support; and a plurality of different aptamer beacons bound to the support, each aptamer beacon having a first end attached to the support, and a binding region that binds to a specific binding site of the target, wherein the binding regions of different aptamer beacons bind to different binding sites. For example, the target can be an antigen, and the different binding sites can be different epitopes of the antigen, or the target can be a bacteria, and the different binding sites can be different surface proteins of the bacteria.

The invention further features a system for simultaneously detecting the presence of a plurality of different non-nucleic acid target molecules in a sample. The system includes a solid support (optional); a plurality of different aptamer beacons, optionally bound to the support, each aptamer beacon having a first end attached to the support, a binding region that binds to a specific non-nucleic acid target molecule, the binding regions of different aptamer beacons binding to different target molecules; and a detection system that detects the presence of target molecules bound to aptamer beacons, the detection system including a radiation source, e.g., a laser, and a detector. The system can further include an analyzer for determining the presence of target molecules in the sample based on the output of the detection system. The analyzer can also include a computer processor programmed to compare the output of the detection system to a library of known outputs corresponding to exposing samples of known composition to the aptamer beacons on the solid support; and select a combination of known outputs that most closely matches the assay outputs. The computer processor can be further programmed to compare any deviation between the output of the detection system and the combination of known outputs to a library of known deviations, the known deviations being caused by known abnormal conditions; and deduce the presence or absence of known abnormal conditions.

In yet another aspect, the invention features a method or system for simultaneously detecting the presence or absence of one or more different target molecules in a sample using a plurality of different species of aptamer beacons, wherein each species of aptamer beacons has a different reporter group, a binding region that binds to a specific non-nucleic acid target molecule, and wherein the binding regions of different aptamers bind to different target molecules; and a detection system that detects the presence of target molecules bound to aptamer beacons, the detection system being able to detect the different reporter groups. The method can also be carried out with a plurality of identical aptamer beacons. For example, each aptamer can include a reporter such as a molecular beacon that changes fluorescence properties upon target binding. Each species of aptamer beacon can be labeled with a different fluorescent dye to allow simultaneous detection of multiple target molecules, e.g., one species might be labeled with fluoroscein and another with rhodamine. The fluorescence excitation wavelength (or spectrum) can be varied and/or the emission spectrum can be observed to simultaneously detect the presence of multiple targets.

The fluorescence measurement can be performed with a number of different instruments, including standard fluorescence spectrophotometers, or in a small volume using a high-intensity source, such a laser, high-efficiency light collection optics, such as a high-numeric aperture microscope objective, and a high-efficiency low-noise detector, such as photo-multiplier tube, a photodiode or a CCD camera.

The method can further include a computer program that includes instructions for causing the processor to compare the measured fluorescence emission or excitation spectrum with the known spectrum of each of the individual dyes to quantitatively determine the concentration of each of the target molecules in the solution.

Different aspects of the invention may include one or more of the following advantages. The aptamer beacon-based detection systems allow the detection of a plurality of different compounds simultaneously, or high sensitivity detection of a single target in a plurality of different ways. Unlike antibodies, which are selected in an organism, the aptamers can be selected in vitro, e.g., in a test tube. This allows detection of target molecules that are toxic or immunologically inert. Unlike standard aptamers, the new aptamer beacons transduce the aptamer:target binding interaction into a detectable change in physical properties of the aptamer beacon.

Furthermore, the aptamer beacons in the detection systems have high affinities for their target molecules, allowing ultra-sensitive detection. As a result, the systems are highly specific, and can distinguish molecules that differ by as little as a single methyl or hydroxyl group.

The systems also allow rapid analysis of a sample (as quickly as a few minutes), facilitating detection of unstable compounds. In addition, the reagents used in the assay are inexpensive, and the chemistry involved in performing the assay is easily automated.

The detection systems can be used in a variety of applications, including drug testing, high-sensitivity testing for the presence of bacteria or antigens, pollution monitoring, and testing for the presence or absence of a disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

Other features and advantages of the invention will be apparent from the following detailed description, and from the claims.

BRIEF DESCRIPTION OF THE DRAWINGS

FIGS. 3A-3D are schematics illustrating two variations of a fluorescence-based reporter system for signaling binding of a target molecule to an aptamer beacon.

FIG. 12 is a schematic illustrating a detection system for use in a solution-based detection method.

FIGS. 13A-D are a series of schematic diagrams of a thrombin aptamer beacon, in various conformations.

DETAILED DESCRIPTION

Figure 1A:
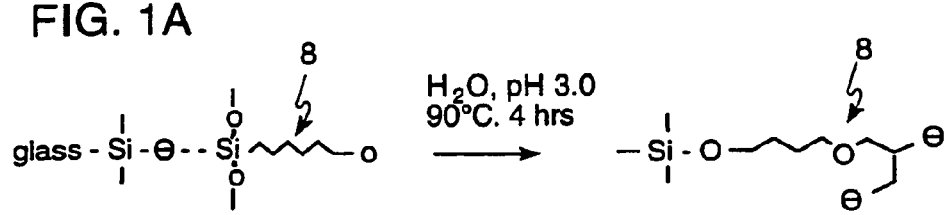
FIGS. 1A and 1B are schematics illustrating a process of attaching an aptamer beacon to glass.

Aptamer beacons are nucleic acids that have been bioengineered to undergo a change in conformation, and thus a detectable change in physical properties, upon aptamer beacon:target interaction. These aptamer beacons can be bioengineered from aptamers that have been selected using well-known aptamer selection techniques. Aptamer beacons can be utilized in either a solution-based detection system or a solid-based, e.g., array, detection system.

The aptamer beacon-based solution detection systems include aptamer beacons configured to bind to specific target molecules and a detection system. The detection system detects binding of target molecules to aptamer beacons by monitoring a change in one or more physical properties, e.g., a change in the fluorescence efficiency, of the aptamer beacons.

The aptamer beacon array-based detection systems include aptamer beacons configured to bind to specific target molecules, a substrate, and a detection system. In these systems, aptamer beacons are attached to the substrate, e.g., in a one- or two-dimensional array. The detection system detects binding of target molecules to aptamer beacons by monitoring a change in one or more physical properties of the aptamer beacons, such as the fluorescence efficiency of fluorescence reporter groups, a change in Raman emissions, or a shift in the conditions required to trigger surface plasmon resonance.

Pattern recognition and analysis software can be used to compare the output of the detection system to outputs caused by known compounds or samples. From these comparisons, the software can, e.g., determine information about the composition of the sample or the condition of the sample source.

Aptamer Selection

Aptamers configured to bind to specific target molecules can be selected, e.g., by synthesizing an initial heterogeneous population of oligonucleotides, and then selecting oligonucleotides within the population that bind tightly to a particular target molecule. Once an aptamer that binds to a particular target molecule has been identified, it can be replicated using a variety of techniques known in biological and other arts, e.g., by cloning and polymerase chain reaction (PCR) amplification followed by transcription.

The synthesis of a heterogeneous population of oligonucleotides and the selection of aptamers within that population can be accomplished using a procedure known as the Systematic Evolution of Ligands by Exponential Enrichment or SELEX. The SELEX method is described in, e.g., Gold et al., U.S. Pat. Nos. 5,270,163 and 5,567,588; Fitzwater et al., "A SELEX Primer," *Methods in Enzymology*, 267:275-301 (1996); and in Ellington and Szostak, "In Vitro Selection of RNA Molecules that Bind Specific Ligands," *Nature*, 346: 818-22. Briefly, a heterogeneous DNA oligomer population is synthesized to provide candidate oligomers for the in vitro selection of aptamers. This initial DNA oligomer population is a set of random sequences 15 to 100 nucleotides in length flanked by fixed 5' and 3' sequences 10 to 50 nucleotides in length. The fixed regions provide sites for PCR primer hybridization and, in one implementation, for initiation of transcription by an RNA polymerase to produce a population of RNA oligomers. The fixed regions also contain restriction sites for cloning selected aptamers. Many examples of fixed regions can be used in aptamer evolution. See, e.g., Conrad et al., "In Vitro Selection of Nucleic Acid Aptamers That Bind Proteins," *Methods in Enzymology*, 267:336-83 (1996); Ciesiolka et al., "Affinity Selection-Amplification from Randomized Ribooligonucleotide Pools," *Methods in Enzymology*, 267:315-35 (1996); Fitzwater, supra.

Aptamers are selected in a 5 to 100 cycle procedure. In each cycle, oligomers are bound to the target molecule, purified by isolating the target to which they are bound, released from the target, and then replicated by 20 to 30 generations of PCR amplification.

Aptamer selection is similar to evolutionary selection of a function in biology. Subjecting the heterogeneous oligonucleotide population to the aptamer selection procedure described above is analogous to subjecting a continuously reproducing biological population to 10 to 20 severe selection events for the function, with each selection separated by 20 to 30 generations of replication.

Heterogeneity is introduced, e.g., only at the beginning of the aptamer selection procedure, and does not occur throughout the replication process. Alternatively, heterogeneity can be introduced at later stages of the aptamer selection procedure.

Various oligomers can be used for aptamer selection, including, e.g., 2'-fluoro-ribonucleotide oligomers, $NH_2$-substituted and $OCH_3$-substituted ribose aptamers, and deoxyribose aptamers. RNA and DNA populations are equally capable of providing aptamers configured to bind to any type of target molecule. Within either population, the selected aptamers occur at a frequency of $10^9$ to $10^{13}$, see Gold et al., "Diversity of Oligonucleotide Functions," *Annual Review of*

*Biochemistry*, 64:763-97 (1995), and most frequently have nanomolar binding affinities to the target, affinities as strong as those of antibodies to cognate antigens. See Griffiths et al., *EMBO J.*, 13:3245-60 (1994).

Using 2'-fluoro-ribonucleotide oligomers is likely to increase binding affinities ten to one hundred fold over those obtained with unsubstituted ribo- or deoxyribo-oligonucleotides. See Pagratis et al., "Potent 2'-amino and 2'fluoro 2'deoxyribonucleotide RNA inhibitors of keratinocyte growth factor" *Nature Biotechnology*, 15:68-73. Such modified bases provide additional binding interactions and increase the stability of aptamer secondary structures. These modifications also make the aptamers resistant to nucleases, a significant advantage for real world applications of the system. See Lin et al., "Modified RNA sequence pools for in vitro selection" *Nucleic Acids Research*, 22:5229-34 (1994); Pagratis, supra.

Bioengineering of Aptamer Beacons

Once aptamers are selected, they are further bioengineered to form aptamer beacons. The aptamers are altered by modifying the primary sequence of the aptamer such that in addition to the binding conformation, the aptamer can now form alternate secondary and/or tertiary non-binding conformations. Aptamers normally fold into active secondary and tertiary structures that facilitate binding, and typically remain in this binding conformation. By changing or adding to the nucleotide sequences of the aptamers to form aptamer beacons, an alternate, non-binding conformation is established that is energetically favored in the absence of a target molecule. In the presence of a target molecule, the binding conformation of the aptamer beacon is favored over the non-binding conformation. In other words, these additional nucleotides are used to allow the aptamer beacon to have one stable, and favored, binding conformation when it contacts and binds to a target molecule, and to have one or more non-binding conformations that do not form the binding conformation in the absence of the target. Stated again, the aptamer beacon can exists in two or more states; target binding acts as a molecular switch between these two states. In addition, the non-binding conformation(s) must not be so stable as to prevent the aptamer beacon from binding to the target. However, once the aptamer beacon binds to a target, the binding conformation is preferably the most favored.

Reporter groups or moieties, including dyes, enzymes, or other reagents, or pairs of reagents, that are sensitive to the conformational change, are also incorporated into the engineered aptamers to form the aptamer beacons. Reporter moieties can be incorporated into the aptamer beacons either prior to transcription or post-transcriptionally, and can potentially be introduced either into known aptamers or into a pool of oligonucleotides from which the desired aptamers are be selected.

Upon binding of the aptamer beacon to a target molecule, the reporter moieties are activated and generate concomitant signals (for example, in the case of a fluorescent dye an alteration in fluorescence intensity, anisotropy, wavelength, or FRET).

Aptamers selected using traditional methods, e.g., SELEX, typically have a known minimum nucleic acid sequence and often have a known binding site. These aptamers are engineered by adding oligonucleotide sequences that typically contain, e.g., 3, 4, 5, 6, or 7 nucleotides, which are complementary to a duplex region of the aptamer, and ideally are complementary to the region of the aptamer that binds to the target molecule, i.e., the aptamer binding region. The preferred aptamer regions to which the complementary oligonucleotides should hybridize can be determined using secondary structure prediction software programs such as M-FOLD™.

These software programs can also be used to compare different hypothetical aptamer beacons. In the preferred embodiment, the free energy predicted for the alternate, unbound form of the aptamer beacon should be less than (i.e., more stable than) the free energy predicted for the bound conformation. This total energy level can be adjusted based on a number of factors, including the base composition and the number of base pairs. Under standard temperature conditions, the complementary oligonucleotide should have no more than 7 nucleotides, because a stem formed of 8 pairs of nucleotides will likely remain in that conformation, and not be able to switch to the target binding conformation.

Once suitable aptamer beacon candidates are prepared, using standard nucleic acid synthesis techniques, they can be tested in a structural determination assay to see whether the desired target molecule modulates the predicted change in conformation. One such structural determination assay is a single strand conformation sensitive gel electrophoresis which can be performed on an 8% acrylamide gel (75:1 bis:acrylamide ratio) including 0.5×TBE (0.045M Tris-borate, 0.002M EDTA pH 8.5) and 10% glycerol. A small volume of radio-labeled aptamer beacon candidates (1 µM) are incubated with or without the target molecule (10 µM) in the binding buffer (typically the same buffer used for aptamer selection). The samples are mixed with an equal volume of 50% glycerol and bromophenol blue (0.05%) and are then loaded on a gel. Electrophoresis is carried out with 300V in a cold room. After the run, the gel is dried and exposed to Kodak X-OMAT film overnight. Results are read from the gel to determine whether the conformation of the aptamer beacon candidate is modulated by the target molecule. Ideally, as can be determined from this aptamer, aptamer beacon candidates should exist in two or more conformations in the absence of the target molecule, and in only one, target-bound conformation, in the presence of the target molecule.

After the aptamers are bioengineered, and optionally analyzed for their conformational changes, one or more reporter groups or moieties, such as fluorescent molecule and quencher pairs as described herein, are added using standard nucleic acid dyes, reagents, and standard synthesis methods. Detection methods described below can then be used to determine the utility of the aptamer.

Aptamer beacons are described herein that undergo a very large change in conformation upon target binding. However, the new methods work equally well with aptamer beacons that undergo small, yet detectable, changes, such as changes typically found in ribozymes.

Attachment of Aptamer Beacons to a Solid Substrate

Solid supports for holding aptamer beacons can be, e.g., a planar sheet of glass, such as a glass slide. Other solid surfaces are also suitable, such as metal, plastic, and ceramic. One technique for attaching aptamer beacons to a glass slide is illustrated in FIGS. 1A and 1B.

Figure 1B:
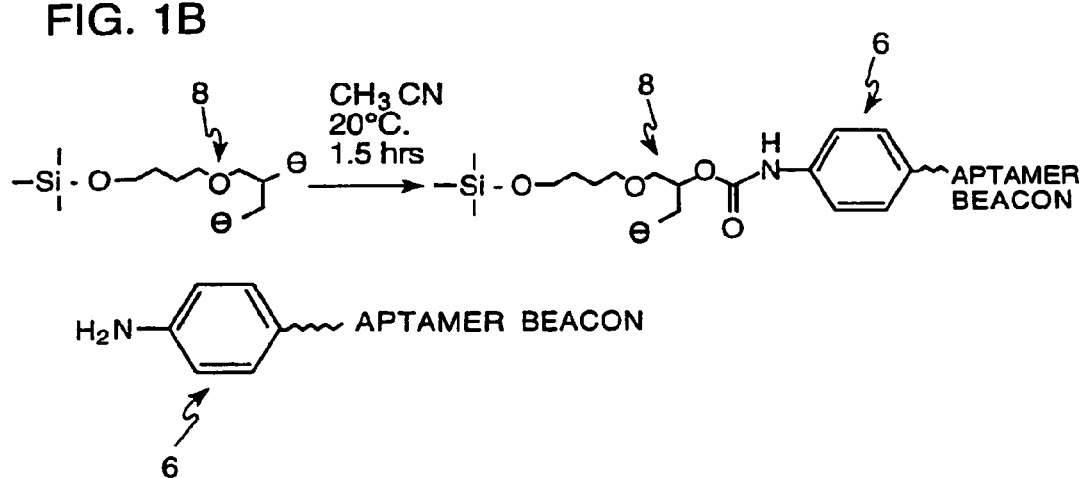

Referring to FIGS. 1A and 1B, an aptamer beacon can be affixed to a glass slide by attaching an amine group of a quencher moiety 6 of the aptamer beacon to the glass via a linker molecule 8. The purpose and attachment of quencher moiety 6 is described below with reference to FIGS. 3A-3D. In the example described in FIGS. 1A and 1B, linker molecule 8 is $C_6O_4Si$, and quencher 6 is $C_6H_4NH_2$. Other known linker molecules and quenchers can be used.

First, linker 8 is attached to the glass slide by dipping the slide into a solution including linker 8 and acidic water (pH 3.0) at 90° C. for four hours (FIG. 1A). After the four hours, linker 8 will coat the surface of the slide. Next, aptamer beacons are attached to the linker molecules on the slide via the amine group of quencher 6. To attach via the amine groups, the coated surface of the glass is exposed to a solution including the aptamer beacon/quencher pair and $CH_3CN$ at 20° C. for 1.5 hours. The aptamer beacons can be localized to a particular spot on the glass slide by applying a microdrop of the aptamer beacon-$CH_3CN$ solution to a precise point on the slide using a robotic micropipetter. See, e.g., Schena et al., "Parallel Human Genome Analysis: Microarray-Based Expression Monitoring of 1000 Genes," *Proc. Nat'l Acad. Sci. USA*, 93: 10514-19 (1996).

Figure 2:
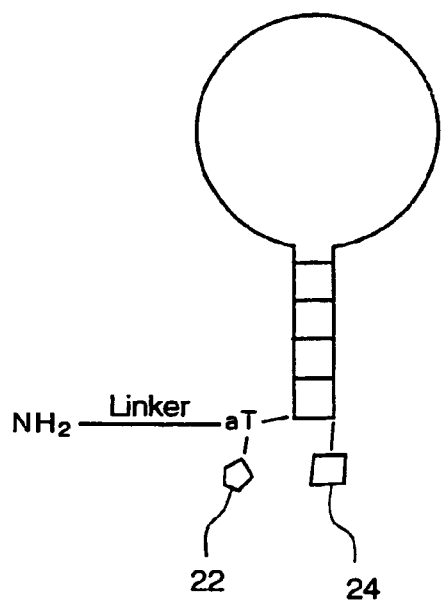
FIG. 2 is a schematic illustrating an aptamer-beacon structure that can be attached to glass using the process shown in FIG. 1.

Referring to FIG. 2, an aptamer beacon having an extended linker can be attached to the glass slide directly, rather than via a quencher. Various known linker molecules can be used. The extended linker can allow the aptamer beacon to extend further into the liquid above the slide, facilitating binding of target molecules. The procedure for attaching the aptamer beacon shown in FIG. 2 is similar to the procedure for attaching the aptamer beacon/quencher of FIG. 1B. (The fluorophore 22 and quencher 24 shown in FIG. 2 will be described below, with reference to FIGS. 3A-3D and 4A-4D.)

Other methods for attaching oligonucleotides to glass are described in Shalon et al., "A DNA Microarray System for Analyzing Complex DNA Samples Using Two-Color Fluorescent Probe Hybridization," *Genome Res.*, 6:639-45 (1996) (oligonucleotides UV crosslinked to a poly-L-lysine coated surface), and Morgan and Taylor, "A Surface Plasmon Resonance Immunosensor Based on the Streptavidin-Biotin Complex," *Biosens. Biolectron.*, 7:405-10 (1992) (aptamers attached using streptavidin).

Different aptamer beacons configured to bind to different target molecules can be attached to different points on the slide. For example, different aptamer beacons can be placed at different points in a two-dimensional array. Each point in the array can contain, e.g., one spot of identical aptamer beacons, applied to the slide as a drop, as described above with reference to FIGS. 1A and 1B. Each spot contains, e.g., about $10^7$ aptamer beacons. Since the spots can be spaced as close as 300 microns apart using a robotic micropipetter, a typical glass slide having a surface area of, e.g., about 1.8 $cm_2$, can hold, e.g., about 6000 spots of different aptamer beacons. See, e.g., Lashkari et al., "Yeast Microarrays for Genome Wide Parallel Genetic and Gene Expression Analysis," *Proc. Nat'l Acad. Sci. USA*, 94:13057-62 (1997).

Related spots of aptamer beacons can be grouped together in clusters on a slide. For example, in drug testing, spots of aptamer beacons configured to bind to the different metabolites of a particular drug, e.g., cocaine, can be grouped together in one region or cluster of the array, and spots configured to detect the metabolites of another drug, e.g., LSD, can be grouped together in a second region. In addition, different spots of aptamer beacons targeted to detect different binding sites on a target, e.g., different epitopes on an antigen, can be grouped together in a cluster. Organizing related spots into clusters in the array can simplify analysis of the results.

Aptamer beacons can also be attached to slides using photoresist masking methods known in the electronics industry. Such techniques, which have already been adapted to DNA oligonucleotide chips for nucleic acid detection, would allow mass production of aptamer beacon arrays having, e.g., about $10^7$ copies of an aptamer beacon at each point in an array, and, e.g., about $6.5 \times 10^4$ points on, e.g., a 1.64 $cm^2$ array. See, e.g., Pease et al., "Light Generated Oligonucleotide Arrays for Rapid DNA Sequence Analysis," *Proc. Nat'l Acad. Sci. USA*, 91:5022-26 (1994).

Detection of Binding of Target Molecules to Aptamer Beacons

A variety of schemes to detect binding of aptamer beacons to target molecules can be employed. First, the reporter moieties of the aptamer beacons can be fluorescent reporters that are monitored, e.g., for changes in fluorescence efficiency. Second, changes in the Raman emission of the aptamer beacons caused by the presence of a target molecule can be observed. Third, shifts in surface plasmon resonances at the surface of the array can be detected by monitoring the change in the wavelength or incident angle of absorbed light, or by using a Mach-Zehnder interferometer. Fourth, the reporter groups or moieties can be enzymes or chemicals that can be monitored for changes in physical properties that occur when the aptamer beacon changes conformation upon binding to a target molecule.

A. Fluorescence Based Detection

To detect binding by monitoring fluorescence emission, fluorophores can be incorporated into reporter moieties of the aptamer beacons. These reporter moieties are configured so that their fluorescence efficiency changes when a target molecule binds to the aptamer beacon and changes the aptamer beacon's conformation, thereby signaling the presence of target molecules in the sample. Fluorescence efficiency can be measured, e.g., using evanescent wave excitation and a cooled CCD camera or single-photon-counting detector.

1. Fluorophore Reporter Moieties

Fluorophore reporter moieties can be, e.g., a fluorescence energy transfer pair that signals a conformation change in an aptamer beacon, or conventional fluorescent labels whose efficiency is dependent on the conformation of the aptamer beacon.

Aptamer beacon reporter moieties can be, e.g., a fluorophore and quencher, as shown in FIGS. 3A-3D, or a charge or energy transfer system, as shown in FIGS. 4A-4D. Referring to FIGS. 3A-3D, aptamer beacons 10a and 10b includes loop portions 12a and 12b, stem portions 14a and 14b, and binding regions (thick black lines) 16a and 16b configured to bind to target molecules 18a and 18b, respectively. In aptamer beacon 10a, the binding region 16a is entirely within loop portion 12a, while in aptamer beacon 10b, the binding region 16b is overlapping loop portion 12b and stem portion 14b.

A reporter moiety or group 20 can include a fluorophore 22 (represented as a pentagon) and a quencher 24 (represented as a square), both attached to stems 14a and 14b. When quencher 24 is in proximity to fluorophore 22, as shown in FIGS. 3A and 3C, fluorophore 22 is quenched, and does not fluoresce significantly upon excitation. When fluorophore 22 and quencher 24 are separated, as shown in FIG. 3B, fluorophore 22 (now represented as a star) fluoresces significantly more efficiently.

Binding of target molecules 18a and 18b to binding regions 16a and 16b breaks base pair binding in stems 14a and 14b, separating fluorophores 22 from quenchers 24. By exciting a fluorophore 22 and determining its fluorescence efficiency, an observer can deduce the presence or absence of a bound target molecule.

Fluorophore 22 can be, e.g., 5-(2'-aminoethyl)aminoapthalene-1-sulfonic acid ("EDANS"), fluorescein, or anthranilamide. Quencher 24 can be, e.g., a chemical group, such as 4-(4'-dimethylaminophenylazo) benzoic acid ("DABCYL"), rhodamine, or eosine.

Fluorophore 22 and quencher 24 can be incorporated into aptamer beacons 10a and 10b using techniques known in the art. See, e.g., Tyagi and Kramer, "Molecular Beacons: Probes That Fluoresce Upon Hybridization," *Nature Biotech.*, 14:303-08 (1996).

Figure 4B:
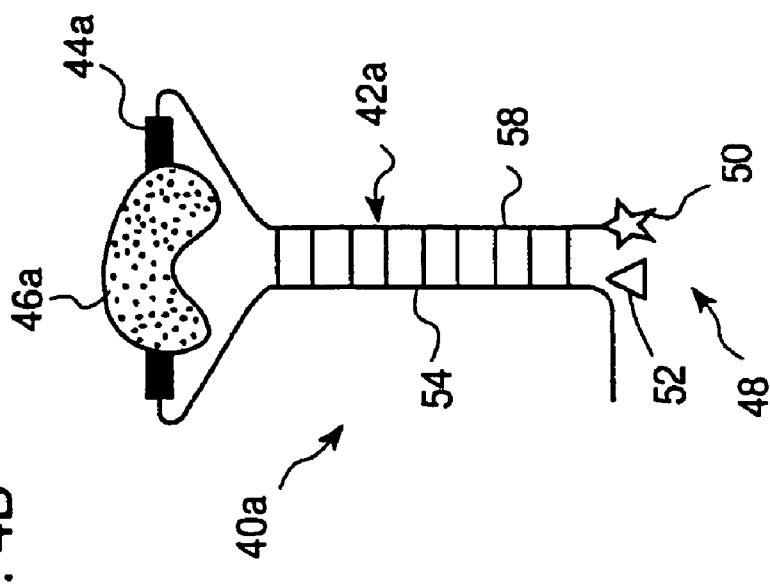
FIGS. 4A-4D are schematics illustrating two variations of an alternative fluorescence-based reporter system for signaling binding of a target molecule to an aptamer beacon.
Figure 4A:
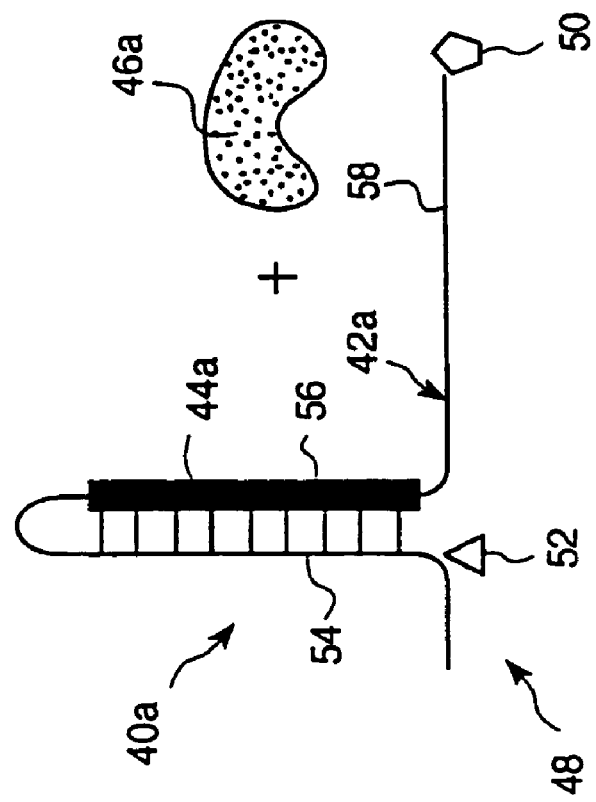

The reporter groups can also include an energy transfer system. Referring to FIGS. 4A-4B, an aptamer beacon 40a has an oligonucleotide 42a with a binding region 44a configured to bind a target molecule 46a. Reporter group 48 includes an acceptor/fluorescence emitting moiety 50 (represented as a pentagon) and a donor/energy absorbing moiety 52 (represented as a triangle) attached to oligonucleotide 42a. When emitting moiety 50 and absorbing moiety 52 are in proximity, as shown in FIG. 4B, energy transfers between the moieties, and emitting moiety 50 (now represented as a star) fluoresces efficiently. When emitting moiety 50 and absorbing moiety 52 are separated, however, as shown in FIG. 4A, no energy transfer occurs between the moieties, and emitting moiety does not fluoresce.

Binding of target molecule 46a to binding region 44a changes the conformation of aptamer beacon 40a by shifting the base pair bindings. When target molecule 46a is not bound to binding region 44a, segment 54 of oligonucleotide 42a hybridizes to segment 56. When target molecule 46a is bound, however, segment 54 hybridizes to segment 58. The change in conformation of aptamer beacon 40a upon binding of target molecule 46a brings emitting moiety 50 and absorbing moiety 52 into close proximity, allowing energy transfer between the moieties, and therefore efficient emission by moiety 50. By monitoring the fluorescence efficiency of reporter 48, therefore, an observer can deduce the presence or absence of a target molecule 46a.

Figure 4C:
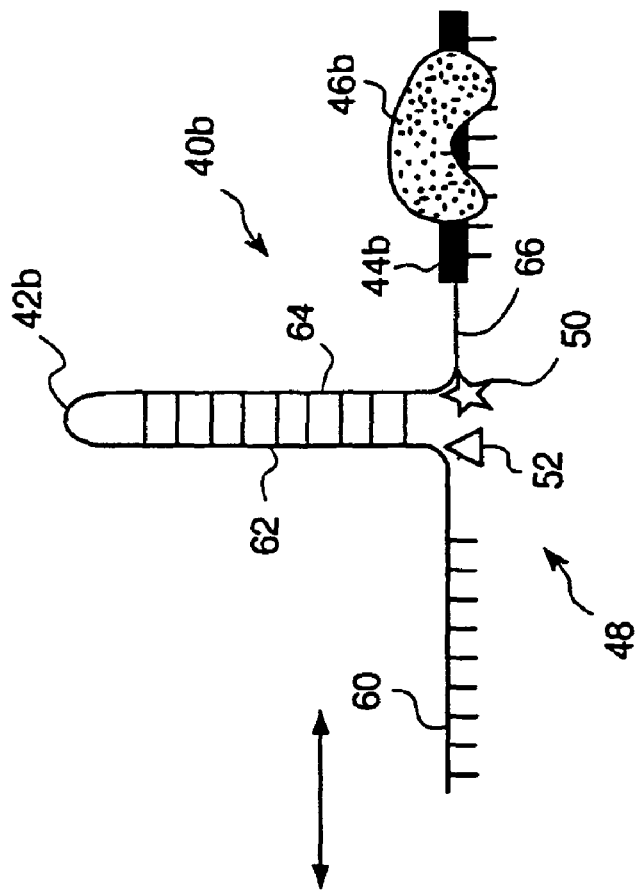
Figure 4D:
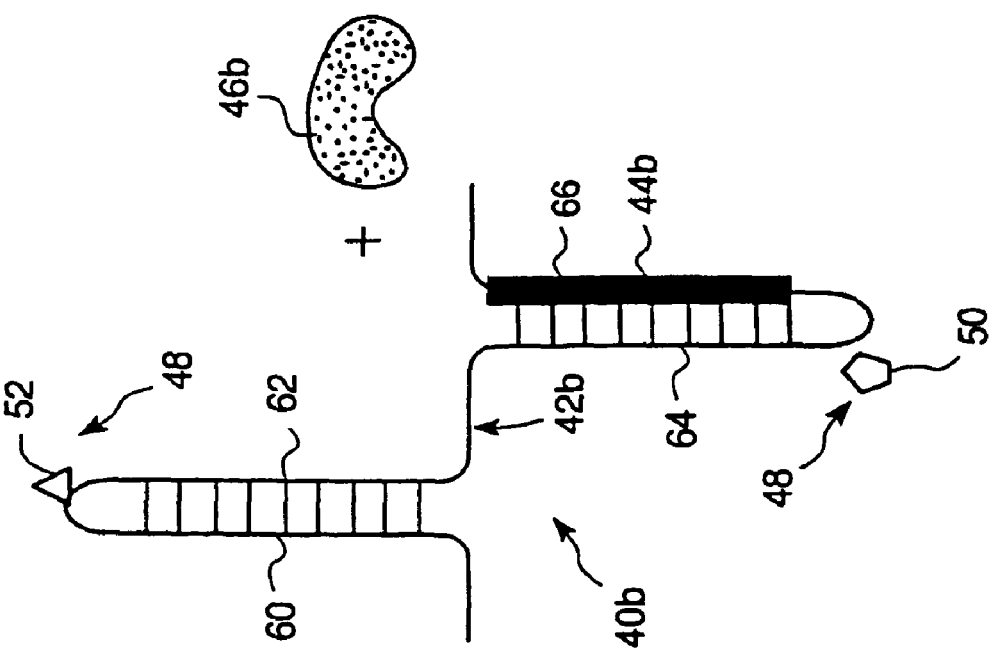

FIGS. 4C-4D illustrate operation of the same energy transfer system on a different aptamer beacon. Aptamer beacon 40b has an oligonucleotide 42b with a binding region 44b configured to bind to a target molecule 46b. Fluorescence emitting moiety 50 and energy absorbing moiety 52 are attached to oligonucleotide 42b. Prior to binding of target molecule 46b to binding region 44b, segment 60 is hybridized to segment 62, and segment 64 is hybridized to segment 66. When target molecule 46b binds, however, aptamer beacon 40b changes conformation, and segment 62 hybridizes to segment 64, and segments 60 and 66 remain unhybridized.

Fluorescence emitting moiety 50 can be, e.g., Cy5. Absorbing moiety 52 can be, e.g., fluorescein or tetramethyl rhodamine ("TMR").

Emitting moiety 50 and absorbing moiety 52 can be attached to oligonucleotides 42a and 42b using techniques known in the art. See, e.g., Sixou et al., "Intracellular Oligonucleotide Hybridization Detected by Fluorescence Resonance Energy Transfer (FRET)," *Nucleic Acids Res.*, 22:662-68 (1994).

Instead of designing aptamer beacons with energy transfer reporters, other fluorescence reporters known in the art can be used. For example, an aptamer beacon can be labeled with a fluorophore whose fluorescence efficiency depends on chemical environment of the molecule to which it is attached. Binding of the target molecule to the aptamer-beacon changes the conformation of the aptamer beacon, thereby changing the chemical environment of the fluorophore, thereby causing a detectable change in the fluorescence of the fluorophore.

2. Surface-Based Fluorescence Detection Systems

A detection system to monitor fluorescence efficiency of reporters can employ evanescent wave excitation to excite the fluorophores, and a cooled CCD camera or a single-photon-counting detector to measure fluorescence.

Figure 5:
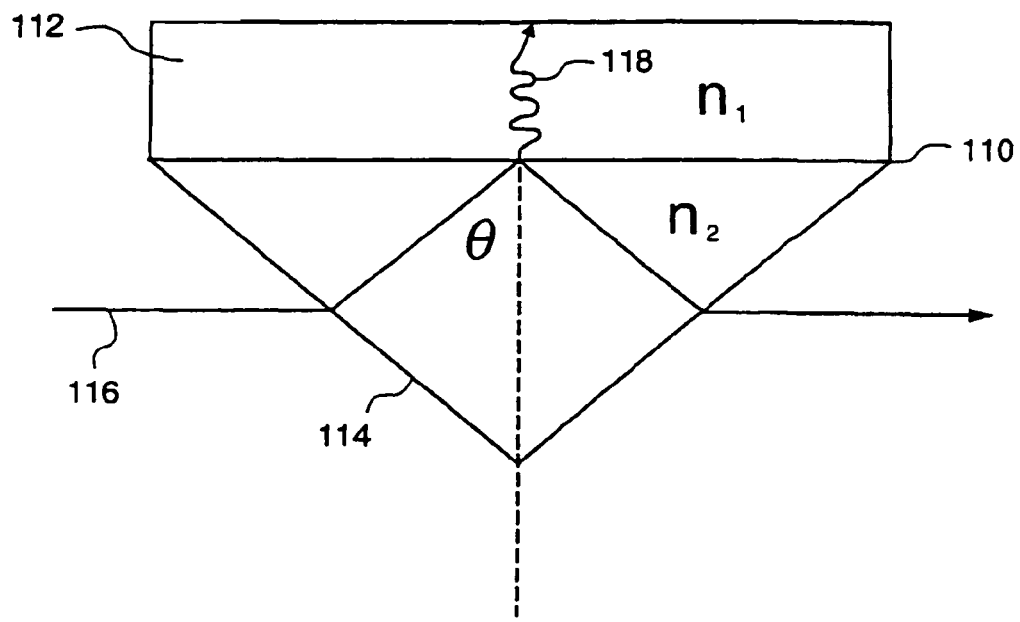
FIG. 5 is a schematic illustrating evanescent wave creation at a total internal reflection boundary.

FIG. 5 illustrates the general principle of evanescent wave excitation. In FIG. 5, a boundary 110 separates a first medium 112 having an index of refraction $n_1$ from a second medium 114 having an index of refraction $n_2$, where $n_2$ is greater than $n_1$. A light ray 116 travels through second medium 114 and approaches boundary 110 at an incident angle of θ degrees. When θ is greater than or equal to the critical angle for total internal reflection, where the critical angle equals arcsin ($n_2/n_1$), the light ray is totally reflected at boundary 110. Despite the fact that the light is totally internally reflected at boundary 110, some energy from a propagating wave 118 enters first medium 112. The wave 118 propagating into medium 112 is called an evanescent wave, and it penetrates into first medium 112 by a wavelength-dependent distance known as the skin depth. The skin depth is a function of the wavelength of the light, the angle of incidence of the beam at the surface, and the refractive indices of both materials. The skin depth is typically on the order of several hundred nanometers for visible light, and decays exponentially away from boundary 110. The evanescent wave 118, therefore, can be used to excite molecules at or near boundary 110 without disturbing molecules beyond the skin depth.

Figure 6:
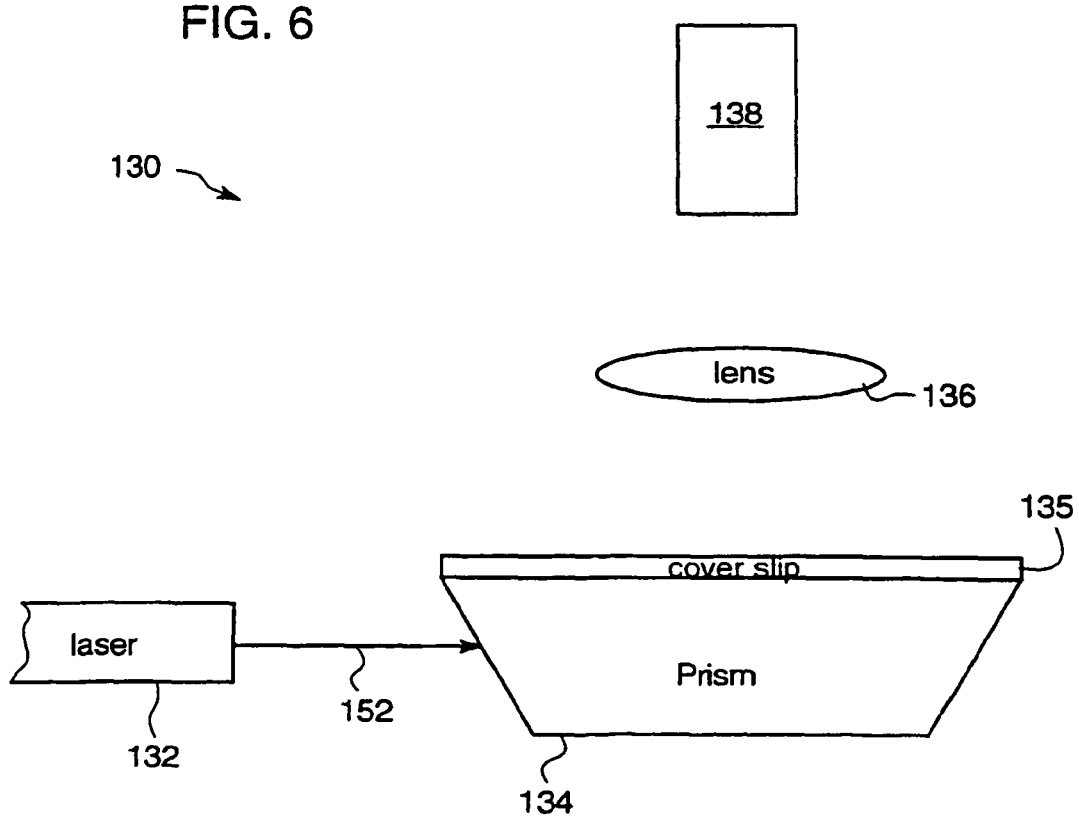
FIG. 6 is a schematic of a detection system for detecting the presence of target molecules bound to aptamers beacons.

Referring to FIG. 6, a fluorescence detection system 130 employing evanescent wave excitation includes a laser 132, an internal reflection prism 134 with a cover slip 135, a lens 136, and a detector 138.

Figure 7:
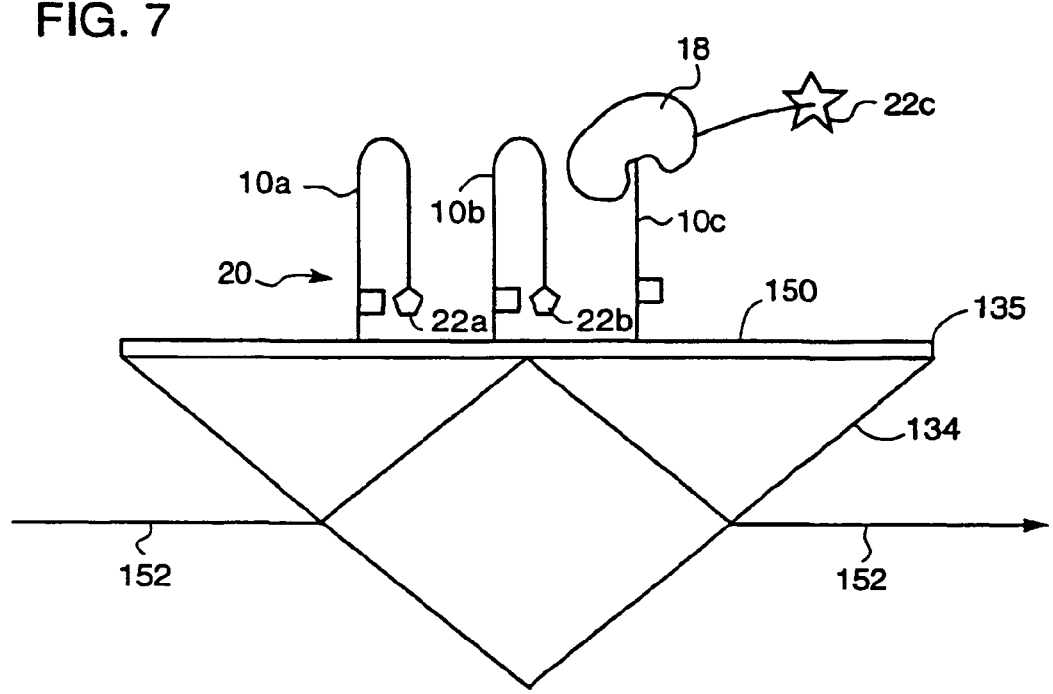
FIG. 7 is a schematic of a prism and cover slip of the detection system of FIG. 6.

Referring to FIG. 7, glass cover slip 135 is affixed to glass prism 134 using, e.g., an index matching liquid, such as an oil, so that no air separates them. Prism 134, cover slip 135 and the oil all have similar indices of refraction, so that no optical boundary exists between prism 134 and cover slip 135.

Cover slip 135 has an upper surface 150 that forms a boundary between a first medium (glass) and a second medium (air). Attached to surface 150 are aptamer beacons 10a, 10b, 10c. Each aptamer beacon 10a, 10b, 10c has a quencher type reporter 20. A target molecule 18 has bound to aptamer beacon 10c, but not to aptamer beacons 10a and 10b.

To excite fluorophores 22a, 22b, and 22c in the reporters 20, a light ray 152 passes into prism 114 and is totally internally reflected at surface 150. An evanescent wave (not shown) travels from surface 150 to aptamer beacons 10a, 10b, 10c, and excites fluorophores 22a, 22b, and 22c. Since fluorophores 22a and 22b are quenched, they will not fluoresce efficiently. Fluorophore 22c, however, is not quenched, and will show greater fluorescence than before binding of target molecule 18. From these results, an observer can deduce that a target molecule 18 has bound to aptamer beacon 10c but not to aptamer beacons 10a and 10b.

Light ray 152 is generated by laser 112. Laser 112 can be, e.g., an argon-ion laser that emits at nine discreet spectral lines between 458 nm and 530 nm, a helium neon laser that emits at 633 nm, or a diode laser that emits at 635 nm. Alternatively, ray 152 can be another form of electromagnetic radiation generated by a source other than laser 112. For example, ray 152 can be infrared, ultraviolet, or microwave.

Figure 8:
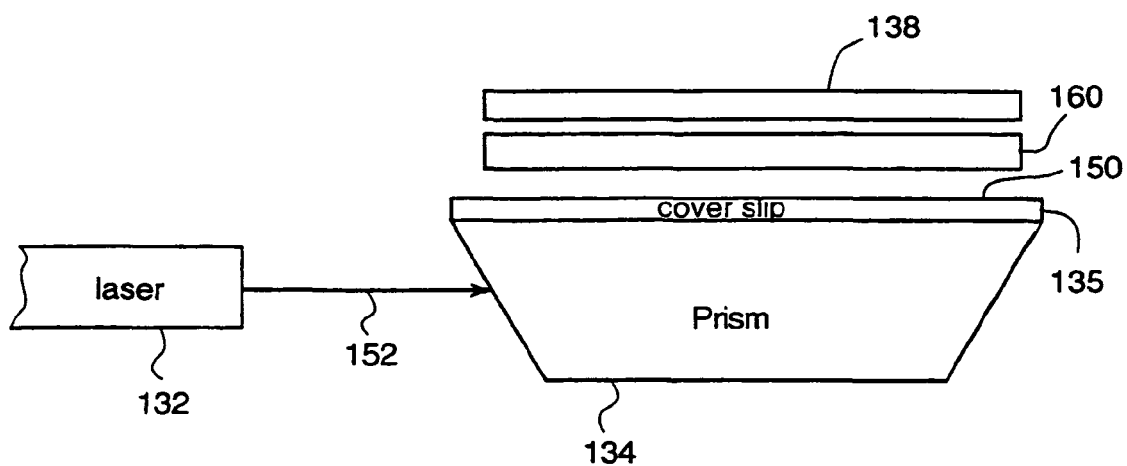
FIG. 8 is a schematic of an alternative detection system for detecting the presence of target molecules bound to aptamer beacons.

As shown in FIG. 6, detector 138 is optically coupled to cover slip 135 by lens 136. Lens 136 serves the same purpose as a lens in an optical microscope. Alternatively, detector 138 can be coupled to cover slip 135 by a fiberoptic coupler 160, as shown in FIG. 8. The input of fiberoptic coupler 160 is in close proximity to surface 150.

Detector 138 is, e.g., a cooled CCD camera or a single-photon-counting detector having, e.g., a confocal microscope. To maximize the ability of detector 138 to discern low levels of fluorescence, background light and stray light should be minimized. Stray light can be reduced, e.g., by adding spectral filters to detector 138 which screen ambient light, and by rastering the array (scanning the array one line at a time to increase spatial discrimination).

3. Solution-Based Fluorescence Detection Systems

A detection system to monitor the fluorescence efficiency of reporter groups of aptamer beacons in solution can include a light source, such as a laser; focusing optics such as a lens;

filters or monochromators to effect changes in the fluorescence excitation or emission spectrum; a chamber to hold the solution; and a cooled CCD camera or a single-photon-counting detector to measure the fluorescence.

FIG. 12 illustrates a detection system 300 for use in solution phase detection methods. A laser 310, such as an argon ion laser can be used as a light source. In this example, the laser light can be filtered with a 488 nM band-pass filter 320 to excite fluorescein labeled reporter groups or with a 514 nM band-pass filter to excite rhodamine labeled reporter groups, allowing the detection of multiple targets. The light then impinges on the sample vessel 330 to excite fluorescence in the sample. The sample vessel could be a cuvette into which solution is placed, or a capillary through which solution is flown. Fluorescence output is then collected by a lens or other light collection optics 340. The fluorescence output is then filtered to remove the excitation light, and optionally to provide target discrimination, using filters 350. In this example, a 515-525 nM band-pass filter could be used to detect fluorescein labeled reporter groups and a 560-580 nM band-pass filter to detect rhodamine labeled targets. In this illustration, the filtered light is then focused by lens 360. Finally, the emitted fluorescence is detected by a cooled CCD or single-photon-counting detector 370.

B. Monitoring Raman Emission

The binding of a target molecule can also be detected by observing a change in the Raman emission of the aptamer beacon. See, e.g., Angel et al., U.S. Pat. No. 4,781,458. The experimental process for measuring Raman emission is similar to the process described above for measuring fluorescence efficiency. Aptamer beacons bound to the surface of a slide or cover slip are excited by an evanescent wave, and the Raman emission is measured using a CCD camera or a single-photon-counter. To isolate the fairly weak Raman emission signals, appropriate cut-off filters can be applied to the detectors.

Both resonant and non-resonant Raman excitation can be used. If necessary, Raman emissions can be enhanced by changing the surface coating of the substrate, e.g., by adding silver, gold, or platinum. See, e.g., U.S. Pat. No. 4,781,458, supra.

C. Monitoring Surface Plasmon Resonances

Binding of target molecules to aptamer beacons can cause localized changes in the index of refraction of the substrate. These localized changes can be measured by monitoring changes in surface plasmon resonances in a thin metal film deposited at the interface between the aptamer beacon solution and the glass substrate.

Electrons in a metal can be modeled as a condensed matter plasma. Free electrons at the surface of the plasma exhibit characteristic density fluctuations, or "surface plasmon oscillations." The surface plasmons can be excited to resonance using, e.g., an evanescent wave. See, e.g., Foster, U.S. Pat. No. 5,485,277. When a totally internally reflected radiation beam excites surface plasmons to resonance, the frequency of the reflected wave is sharply decreased. The precise incident angle which excites surface plasmons to resonance, therefore, can be detected as a sharp decrease in a graph of the energy of the reflected wave as a function of the angle of incidence.

When target molecules bind to aptamer beacons attached to a thin metal film, the local index of refraction at that point changes, shifting the particular wavelength and/or angle of incidence required to excite the surface plasmons to resonance. The binding of a target molecule to an aptamer beacon (or the binding of a large number of identical target molecules to identical aptamer beacons in an aptamer beacon spot in an array), therefore, can be detected by observing either a shift in the wavelength or the incident angle required to excite surface plasmons to resonance.

A system to detect binding of target molecules to aptamer beacons by measuring shifts in surface plasmon resonance conditions can include, e.g., a quartz prism with a silver film deposited thereon by vacuum evaporation. For surface plasmon resonance detection, a beam is focused into the prism so that a cone of incident angles can be measured simultaneously. The totally internally reflected beam is collimated and imaged on, e.g., a CCD camera. The resonant angular condition appears as a dark band in the beam profile. Binding of target molecules to aptamer beacons causes a shift in the resonant condition, which translates into a spatial shift in the dark band in the beam profile.

Changes in surface plasmon resonance conditions can also be observed using a Mach-Zehnder interferometer (MZI). In an MZI, a coherent beam is launched down two equal path-length legs, resulting in total destructive interference of the beam at an output where the two beams recombine. Changing the effective length of one of the legs, e.g., by altering the index of refraction at a point in the leg, destroys the destructive interference condition. MZI's are sensitive to path length changes as small as fractions of the wavelength of the incident light. See, e.g., Kusunose et al., U.S. Pat. No. 5,771,097.

An MZI having single-mode optical fibers that act essentially as waveguides can be constructed to detect binding of target molecules to aptamer beacons. The metal film coating in which surface plasmon oscillations are induced is deposited along the lengths of the fiber optic waveguides, and the aptamer beacons are attached to the film coating.

The MZI will initially be adjusted so that the beam triggers surface plasmon resonance in the leg having the film coating, and the two legs recombine out of phase, resulting in total destructive interference. Binding of target molecules to the aptamer beacons on the film coating, however, will change the resonance condition in that leg and destroy the conditions for total destructive interference at the output of the interferometer. Thus, detecting light at the output will indicate that target molecules have bound to aptamer beacons on one leg of the MZI. Measuring the intensity of the recombined light can indicate the quantity of target molecules that have bound.

D. Other Detection Schemes

Other schemes to detect binding of target molecules to aptamer beacons can also be used. For example, reporter groups other than fluorophores can be incorporated into aptamer beacons. The reporter groups can signal a conformational change in the aptamer beacon caused by binding of the target molecule, or can interact with the target molecule in a manner that changes the nature of the target. Such reporters can be, e.g., a charged moiety that transfers energy to a bound target. Examples of these reporters include protein enzymes.

The aptamer beacons can be attached to conductive polymers, in which binding of a target molecule to the aptamer beacon, and the resultant change in conformation of the aptamer beacon, causes a conformational change in the polymer, altering the conductivity. The change in conductivity could be determined, e.g., by measuring a resistance across the polymer.

In another method, the aptamer beacon can be designed to catalyze a chemical reaction upon the change in conformation induced by binding of a target molecule. Presence of a bound target molecule could then be deduced by detecting products of the reaction.

Figure 9A:
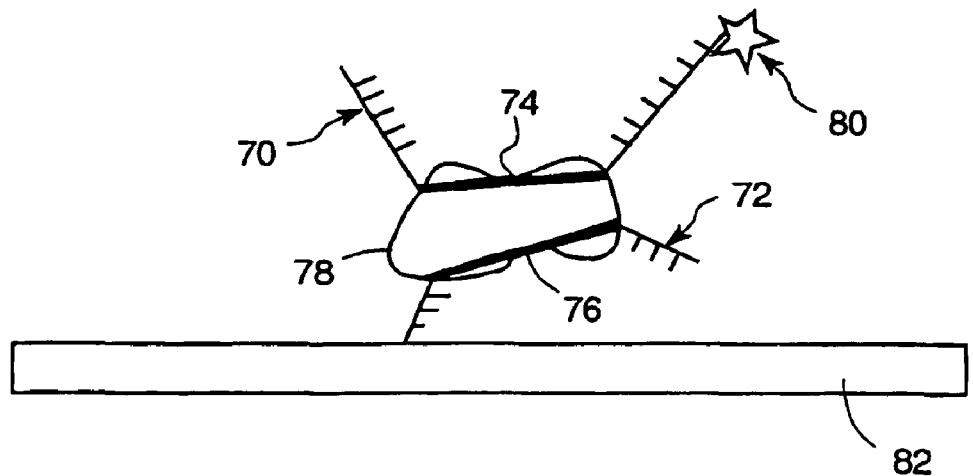
FIG. 9A is a schematic illustrating a two part aptamer beacon detection strategy that employs two different nucleic acids configured to bind to different binding sites on a target molecule.

The presence of target molecules can be detected using a two-component aptamer beacon system. Referring to FIG. 9A, aptamer beacon components 70 and 72 have binding regions that bind to separate (e.g., different) binding sites 74 and 76 on a target molecule 78. Aptamer beacon component 70 has a fluorescent label 80, while aptamer beacon component 72 is attached to glass substrate 82. Note that for solution-based measurements it is not necessary to attach 72 to 82.

To detect the presence of target molecule 78 in a sample, the sample is first mixed with a solution that includes aptamer beacon component 70. If target molecules 78 are present, they will bind to binding sites 74 on aptamer beacon component 70. Next, the sample/solution mixture is exposed to substrate 82. The target molecules will then bind to aptamer beacon component 72 on the substrate via binding sites 76. The presence of target molecules 78 bound to aptamer beacon component 72 can then be detected by observing fluorescence of label 80. Alternatively, the target molecules 78 in solution can be added to a container, or poured or dropped onto a solid substrate 82, such as a glass slide, to which aptamer beacon components 72 are bound. Any unbound target molecules 78 are washed away, and then labeled aptamer beacon components 70 are added to the container or solid support, where they bind to any target molecules 78 bound to the solid substrate 82 by aptamer beacons 72.

Figure 9B:
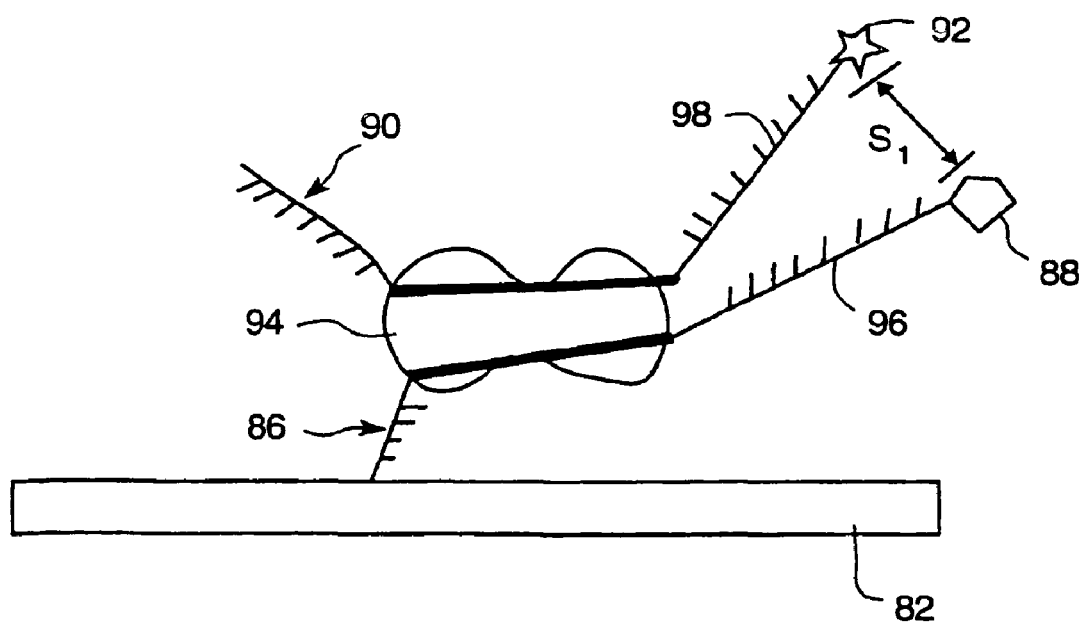
FIG. 9B is a schematic illustrating an alternative two part aptamer beacon detection strategy employing two different nucleic acids configured to bind to different binding sites on a target molecule.

FIG. 9B illustrates another two-component aptamer beacon detection system. In FIG. 9B, aptamer beacon component 86, bound to substrate 82, has an energy absorbing moiety 88 attached to segment 96, and aptamer beacon component 90 has a fluorescence emitting moiety 92 attached to segment 98. Binding of both aptamer beacon components 86 and 90 to a target molecule 94 brings segment 96 into proximity with segment 98, allowing an energy transfer between the moieties, thereby causing the fluorescence emitting moiety 92 to emit fluorescence, as discussed above with reference to FIGS. 4A-4D. Energy will transfer from absorbing moiety 88 to emitting moiety 92 as long as the distance $S_1$ between the moieties is less than 100 Å.

To improve the efficiency of the energy transfer between absorbing moiety 88 and emitting moiety 92, segments 98 and 96 can be configured to hybridize to each other when aptamer beacon components 90 and 86 are both bound to target molecule 94. For example, to enable hybridization, poly-A and poly-T tails can be added to segments 98 and 96, respectively. Alternatively, more complicated complementary sequences can be added to segments 98 and 96, to reduce the likelihood that other polynucleotides, e.g., polynucleotide tails on other aptamer beacons, will hybridize non-specifically to segments 98 and 96.

In addition, mass spectroscopy, separately or in conjunction with the above detection systems, can be used to further identify or further quantify bound target molecules.

Other detection systems are also within the scope of the claims.

Use and Interpretation of Aptamer Beacon Arrays

The assay systems described above can be used in a variety of different fields, including, e.g., testing for performance enhancing or illegal drugs in humans or animals; testing food for poisons, contaminants, additives, or genetically engineered components; forensic testing; general health checkups; identifying specific diseases and monitoring the progression of a disease, e.g., cancer; detecting pollutants and tracing polluters; assaying environmental balance (healthy rivers, lakes, wetlands, soil, and air); detecting biohazards; detecting chemical poisons or chemicals; detecting explosives or illegal drugs, for example in airports; detecting pollen and other allergens in the environment; detecting the presence of particular types of animals or fish in specific environments, e.g., sharks in a bathing area, trout in a lake or stream; and target identification for drug discovery.

In addition to simultaneously testing a sample for the presence of a plurality of different targets, the array can also test for the presence of a single target by binding to the target in a plurality of different ways. Such a test would have greater sensitivity than conventional target molecule assays.

For example, an aptamer beacon array can be constructed having different spots of aptamer beacons configured or selected to bind to different binding sites of a single target. The different aptamer beacon spots can, e.g., be configured to bind to different epitopes of a single antigen, to different binding sites on the same protein, or to different surface proteins of a single bacteria. The different spots containing aptamer beacons designed or selected to bind to different binding sites on the same target can be grouped together in a cluster. If the detection system shows that targets have bound to all or nearly all the aptamer beacon spots in such a cluster, then an observer can conclude with great confidence that the target is present in the sample.

Similarly, aptamer beacon arrays or clusters of aptamer beacon spots can be constructed to test for different enantiomers of a molecule, or different isomers of a molecular formula.

Figure 10A:
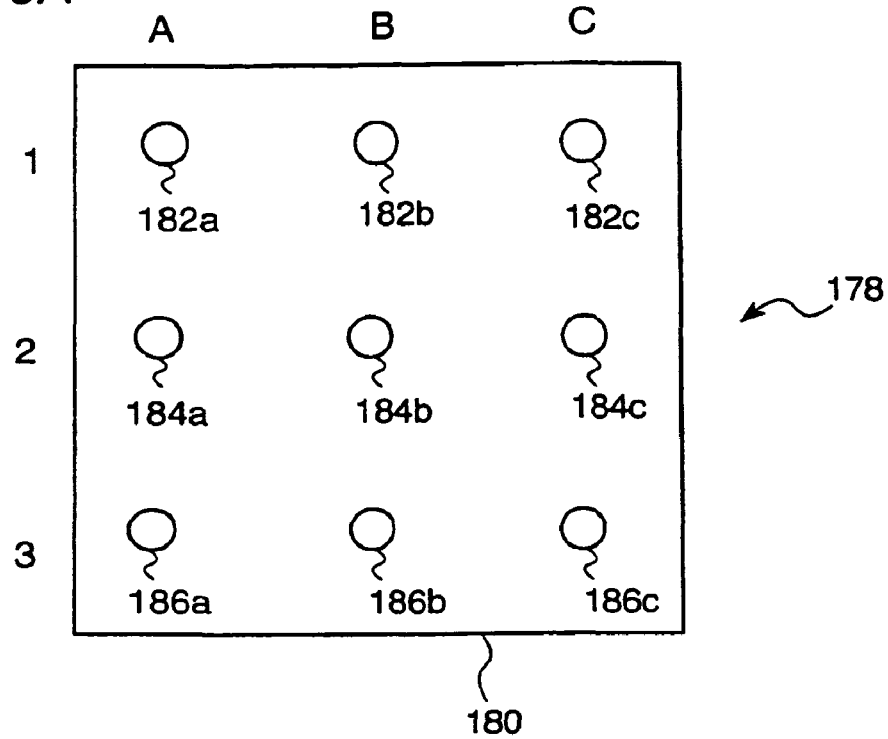
FIG. 10A is a schematic of an aptamer beacon array.
Figure 10B:
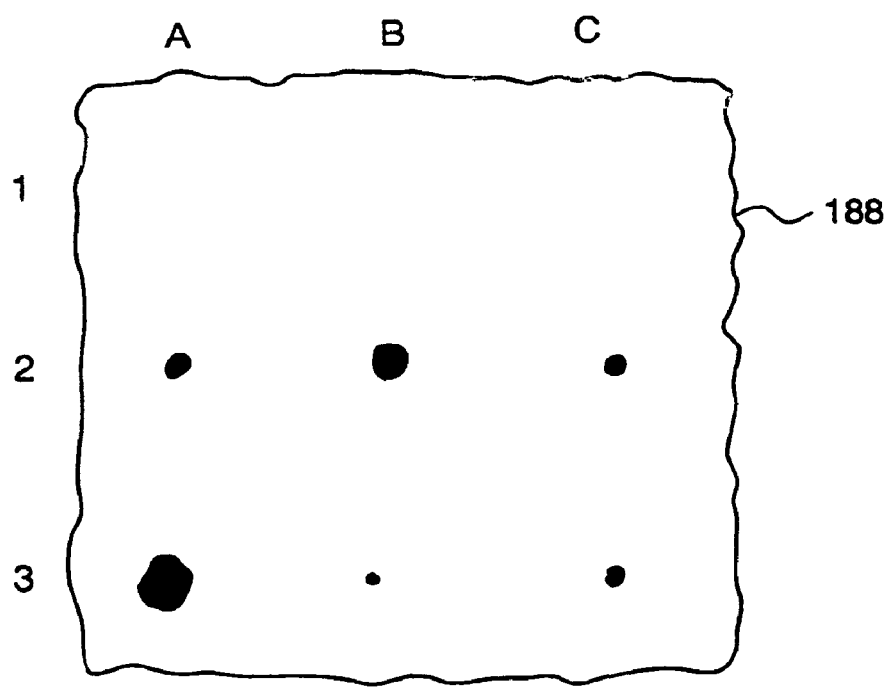
FIG. 10B is a schematic of an image showing fluorescence in the aptamer beacon array of FIG. 9A after exposure of the array to a sample.

FIGS. 10A and 10B illustrate the use and interpretation of a simple aptamer beacon-based assay for detecting harmful poisons in food. Referring to FIG. 10A, an aptamer beacon array 178 bound to a cover slip 180 includes nine spots of aptamer beacons, arranged in three rows of three spots each. Spots 182a, 182b, and 182c in row one contain aptamer beacons selected to bind to three different epitopes of *Clostridium botulinum*. Spots 184a, 184b, 184c in row two contain aptamer beacons that bind to three different epitopes of a *Salmonella* bacteria. Spots 186a, 186b, 186c in row three contain aptamer beacons selected to bind to three different preservatives naturally found in a particular food. The preservatives, however, can be harmful if present in too high a quantity. Each spot contains, e.g., about $10^7$ identical aptamer beacons. Each aptamer beacon includes a fluorophore-quencher pair, as described above with reference to FIGS. 3A-3D.

In operation, the food to be tested is dissolved in a solvent, e.g., water, and placed into contact with cover slip 180. Cover slip 180 is then placed atop a total internal reflection prism, and the fluorophores in the aptamer beacons are excited using evanescent wave excitation, as described above with reference to FIGS. 5-7. A CCD image 188 of the array after excitation is shown in FIG. 10B.

The results of the assay can be interpreted by visual inspection. The absence of fluorescence by spots 182a, 182b, and 182c suggest that *Clostridium botulinum* is not present in the sample. Fluorescence by spots 184a, 184b, and 184c, however, suggest that *Salmonella* is present.

Spots 186a, 186b, and 186c, which are targeted to preservatives normally found in the food, all fluoresce, as expected. The amount of fluorescence in each cluster, however, can be analyzed to determine the concentration of each preservative present in the sample. If the sample has a higher concentration of a preservative, more preservative molecules will bind to aptamer beacons in the corresponding spot, resulting in a greater total fluorescence of the spot. For example, in FIG. 10B, spot 186a fluoresces more than spots 186b and 186c, indicating a higher concentration of that particular preservative.

To determine visually if the concentration of a preservative is dangerously high, the brightness of a particular spot, e.g., the fluorescence associated with spot 186a, can be compared to a template showing fluorescence levels for normal concentrations. In addition, to obtain more quantitative data, concentration "curves" or control studies for each preservative (or each target molecule for that matter) can be established using the aptamer beacon system, and samples of a given preservative (or other target) at several known concentrations that vary from high to low.

Pattern Recognition and Analysis Software

In using the aptamer beacon array described above with reference to FIGS. 10A and 10B, the results of the assay can be determined simply by visual inspection. As noted above, however, more complicated aptamer beacon-based assays can have tens or thousands of spots of aptamer beacons in two-dimensional arrays. Other arrays, e.g., 3-D, can be made. The results of such an assay might not be easily apparent by visual inspection.

To assist in analyzing the results of more complicated assays, new pattern recognition and analysis software can be used, as described below.

In brief, the software first analyzes the output from the detection system to determine the identities and quantities of compounds present in the sample. Next, the software compares the list of compounds present in the sample to lists of compounds expected to be present under normal conditions, and notes any deviation. The software then attempts to interpret and decipher or explain the deviation by comparing the deviation to a library of known assay results.

For example, in testing the blood of a 21-year old female for illegal drugs using, e.g., a fluorescence based detection system, the software first analyzes the fluorescence pattern formed on a slide after the slide is exposed to the blood sample. By noting which aptamer beacon spots fluoresce, and how much they fluoresce, the software determines what compounds are present in the sample, and in what quantities. The software then compares the compound list to a list of compounds expected to be present in the blood of a 21 year-old female not using drugs, and determines any deviation. The deviation found is compared to deviations known to be caused by the presence of illegal drugs, e.g., cocaine. The software then tests the results for significance, and displays a list of illegal drugs present.

Figure 11A:
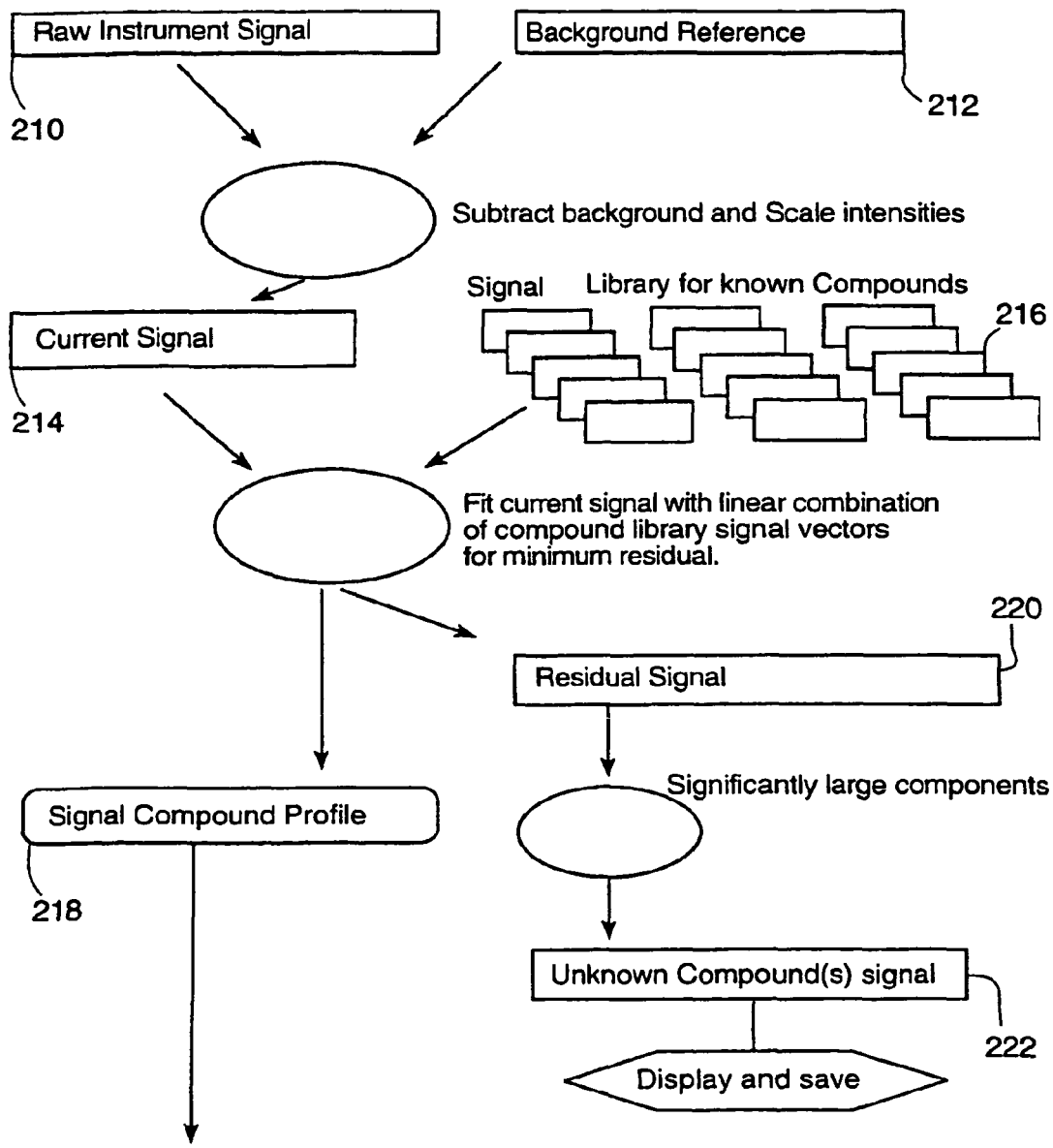
FIGS. 11A and 11B are flow charts of a process for detecting patterns in the output of a detection system.
Figure 11B:
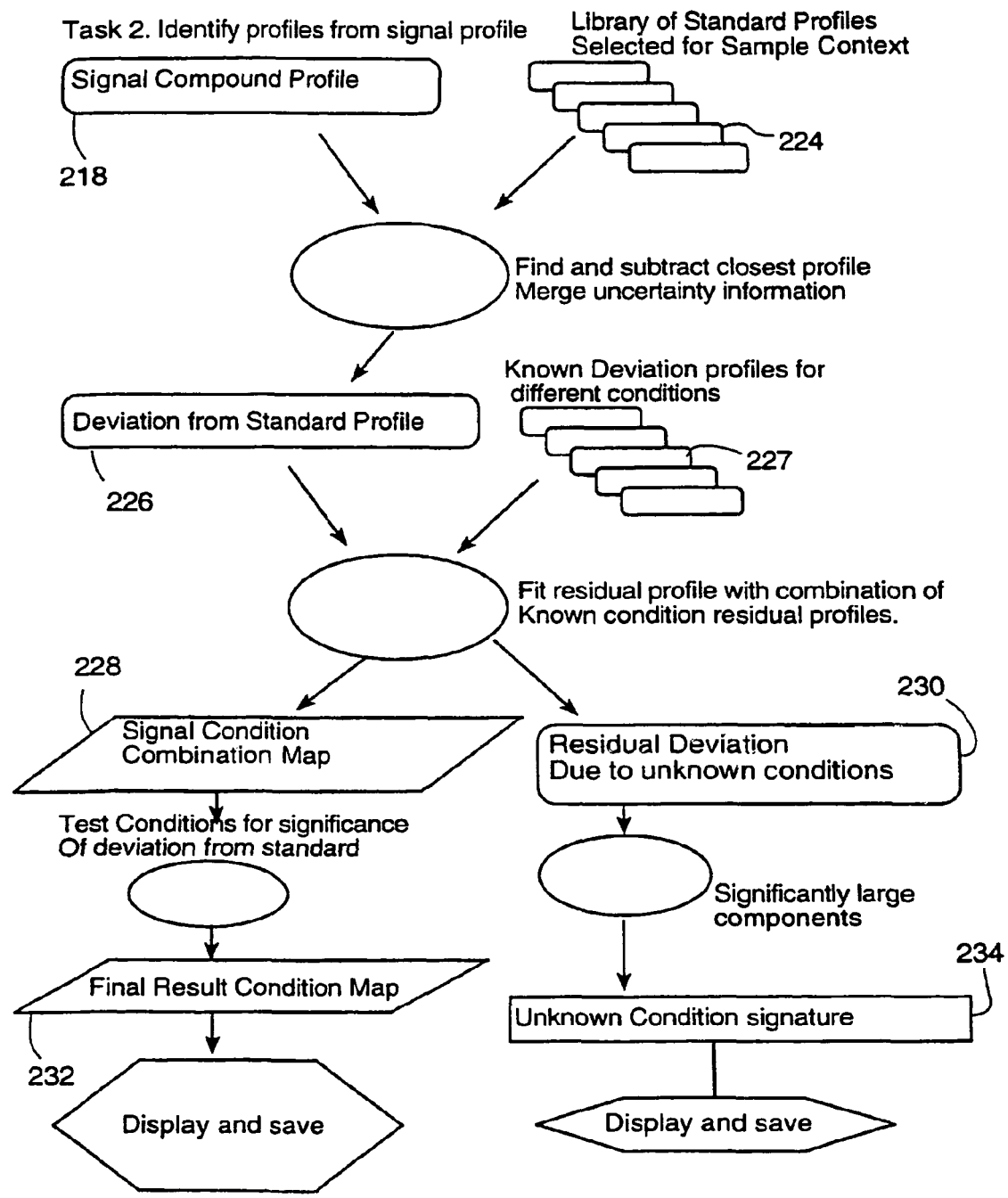

FIGS. 11A and 11B illustrate the pattern detection process. FIG. 11A illustrates the steps and execution of the software's first task, determining the identity and quantity of compounds present and building a list, or a Signal Compound Profile, and FIG. 11B illustrates the steps and execution of the software's second task, comparison of the Signal Compound Profile to known profiles.

Referring to FIG. 11A, the software first receives the output from the detection system, typically an image, and converts the image into a digital Raw Instrument Signal 210. To convert the image into a digital signal, the software divides the image into sectors, each sector corresponding, e.g., to one aptamer beacon spot in the array, and converts the intensity of the signal in the sector to a digital representation. The digital representations of the sectors are stored, e.g., as a matrix.

A Background 212 is then subtracted from Raw Instrument Signal 210 to eliminate portions of the output that are not of interest (i.e., background noise). For example, in testing river water for pollutants dispersed by a nearby factory, for example, Background 212 can be the output that results when river water upstream from the factory is exposed to the aptamer beacon array. The data that results from subtracting the Background 212 is Current Signal 214.

Current Signal 214 is then compared to a Signal Library 216 of digital signals. Signal Library 216 includes the signals that result from exposing the same array to specific known compounds. The software compares Current Signal 214 with different combinations of signals in Signal Library 216 to find the combination of known compound signals that most closely matches Current Signal 214. The software determines the closest match, or the fit with the smallest residual, using, e.g., a least squares fitting method, or known linear or non-linear deconvolution techniques, such as maximum-likelihood and maximum-entropy methods. The result of the comparison is two separate outputs: Signal Compound Profile 218 and Residual Signal 220.

Signal Compound Profile 218 is a list of the library compounds present in the sample, the quantities of each compound present, and associated uncertainty estimates. Signal Compound Profile 218 can be stored, e.g., as a matrix. Residual Signal 220 is the component of Current Signal 214 not accounted for by the chosen combination of signals from Signal Library 216.

Residual Signal 220, like Raw Instrument Signal 210 and Current Signal 214, can be, e.g., a matrix. Residual Signal 220 is tested for significance by comparing each element in the matrix to the uncertainty level for corresponding elements in Current Signal 214. Elements found to be significant are labeled as Unknown Compounds Signal 222, displayed, e.g., on a monitor, and stored.

Referring to FIG. 11B, the software next compares Signal Compound Profile 218 to one or more standard profiles from Standard Profile Library 224. Each standard profile in Standard Profile Library 224 is a list of the types and quantities of compounds expected if no unusual conditions are present (i.e., the assay result is negative). For example, in analyzing a blood sample from a 21 year-old female for drug testing, the relevant standard profile would be the list of compounds expected for testing blood from a normal 21 year-old female not using drugs. In testing river water for pollutants, a relevant standard profile would be the compounds ordinarily found in water taken from a particular point in the river at the season and temperature in question.

In many cases, Signal Compound Profile 218 will be compared to more than one standard profile in Standard Profile Library 224. The standard profiles can also include uncertainty information, e.g., standard deviations, that might be expected from a statistical sample of the relevant standard profiles under normal conditions.

In some cases, the relevant standard profiles in Profile Library 224 will be chosen in advance by a user. In other cases, the most applicable standard profiles will be chosen by the software by determining which combination of standard profiles is closest to Signal Compound Profile 218.

After choosing the appropriate standard profiles from Profile Library 224, the software subtracts these profiles from Signal Compound Profile 218 to create Deviation from Standard Profile 226. Like Signal Compound Profile 218, Deviation 226 is a list of compounds and quantities, stored, e.g., as a matrix.

Deviation 226 is then compared to Known Deviations Library 227. Each known deviation in Deviation Library 227 is the deviation from standard profiles expected for a particular assay result. In drug testing, for example, a known deviation can be a list of additional metabolites found in blood when cocaine is present in a blood sample. For performance enhancing steroids, the known deviation can include the difference between normal and elevated testosterone levels. In water pollution testing, a known deviation can be the deviation expected if a nearby factory is dumping trichloroethylene into a stream.

The software compares Deviation 226 with different combinations of known deviations in Deviation Library 227 to find the combination that most closely matches Deviation 226. As before, the closest match, or the fit with the smallest residual, can be found using, e.g., the least squares fitting method.

The comparison of Deviation 226 with Known Deviation Library 227 yields two outputs: Signal Condition Combination Map 228 and Residual Deviation 230. Signal Condition Combination Map 228 includes the list of known deviations found by comparing Deviation 226 with Deviation Library 227. For example, in drug testing, Combination Map 228 can be a list of illegal drug compounds or metabolites of illegal drug compounds present, and the quantities in which they are present. The results listed in Combination Map 228 are tested for statistical significance by considering the uncertainty data in Deviation 226 and range limits in the known deviations found to be present. The results in Combination Map 228 found to be significant are displayed and/or stored as the Final Result Condition Map 232. In drug testing, for example, Condition Map 232 might list metabolites of illegal drugs present in the sample, or it might identify the illegal drugs the individual likely ingested. In water pollution testing, the Condition Map might list pollutants being released by a nearby factory.

Residual Deviation 230 is the compound identities and quantities not explained by a combination of known deviations in Deviation Library 227. Residual Deviation 230 is screened for significance, and then displayed and/or stored as Unknown Condition Signal 234. Unknown Condition Signal 234 is the list of compounds and quantities found, but not explained by any known assay results.

The software can be trained to identify new compounds in Residual Signal 220, and new patterns in Residual Deviation 230. By analyzing covariation of signal components across multiple samples collected at different times or places, the software can learn to create new standard profiles and new known deviations. The software can be trained, e.g., with differential analysis using, e.g., the sample with the minimum vector modulus as the reference background.

The methods and techniques described herein can be implemented in digital electronic circuitry, or in computer hardware, firmware, software, or in combinations thereof. Apparatus embodying these techniques may include appropriate input and output devices, a computer processor, and a computer program product tangibly embodied in a machine-readable storage device for execution by a programmable processor. A process embodying these techniques can be performed by a programmable processor executing a program of instructions to perform desired functions by operating on input data and generating appropriate output. The techniques can be implemented in one or more computer programs that are executable on a programmable system including at least one programmable processor coupled to receive data and instructions from, and to transmit data and instructions to, a data storage system, at least one input device, and at least one output device.

Each computer program can be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including, e.g., semiconductor memory devices, such as EPROM, EEPROM, and flash memory devices; magnetic disks such as internal hard disks and removable disks; magneto-optical disks; and CD-ROM disks. Any of the foregoing may be supplemented by, or incorporated in, specially-designed ASICs (application-specific integrated circuits).

The computer program and method described above can be adapted to analyze the results of biological assays other than the aptamer beacon-based detection system described herein. The method and software can be applied to any biological assay designed to detect the presence of known compounds in a sample.

EXAMPLES

The invention is further described in the following Examples, which do not limit the scope of the invention described in the claims.

Example 1

Drug Testing

In this Example, a blood sample drawn from a 26 year-old athlete is tested for the presence of performance enhancing drugs.

First, a microarray slide targeted to test for the presence of several dozen known performance enhancing drugs, including androstenedione, amphetamines, testosterone based steroids, and other drugs, is prepared. Metabolites of the drugs are identified from literature and experimentation.

The aptamer selection procedure is performed in a physiological saline buffer to select aptamers that bind to the drugs directly and to metabolites of the drugs. The aptamers selected are RNA aptamers between 25 and 150 nucleotides in length, having binding sequences between 15 and 60 nucleotides in length. Standard aptamer selection techniques are used to determine the minimum binding sequence. The selected aptamers are then engineered to contain a stem loop structure as shown in FIG. 3. DABCYL and EDANS are added to the 5' and 3' ends aptamers to create an aptamer beacon with a fluorophore reporter system, and the aptamer beacons are then attached to a glass slide in a two-dimensional array, in the manner described above with reference to FIG. 2.

The athlete's blood sample is then dissolved in the same saline buffer used to carry out the aptamer selection, and a drop of the buffer-blood sample solution is applied to the slide. The sample solution drop entirely covers the aptamer beacon array on the slide.

Exposure to the sample allows any drugs or metabolites in the sample to bind to aptamer beacons in the array. Binding of the metabolites causes a conformational change in the aptamer beacons that results in fluorophore quenchers being separated from the fluorophores, as described above with reference to FIGS. 3A and 3B.

After exposure to the sample, the slide is placed on a total internal reflection prism. To optically couple the slide to the prism, an oil (such as LASER LIQUID from Cargille Laboratories, Inc., N.J.) having an index of refraction approximately equal to the index of refraction of the glass slide and glass prism, is placed on the prism below the slide. The oil ensures that no air pockets form between the slide and the prism.

A laser of appropriate wavelength is then applied to the prism such that the laser beam approaches the slide at an incident angle approximately equal to the critical angle for total internal reflection. The beam is totally internally reflected at the top of the slide (the boundary between glass and air), creating an evanescent wave that excites unquenched fluorophores in the aptamer beacon array. The fluorescence pattern resulting from the evanescent wave excitation is imaged using a cooled CCD camera.

The image captured by the CCD camera is compared to a template or library of fluorescence patterns of known compounds to determine the metabolites present. By examining which aptamer beacon spots in the array fluoresced, the technician is able to identify a list of metabolites present in the blood sample. From this list, the technician can conclude whether the athlete recently ingested any specific legal or illegal drugs such as steroids.

Example 2

Thrombin Aptamer Beacons in Solution

Thrombin aptamer beacons were designed and tested in solution for their specificity to thrombin by itself and compared to Factor IX. The addition of several different sets of oligonucleotides to the 5' end of a known thrombin aptamer, G15D, formed a group of bioengineered aptamer beacons that are designed to exhibit alternate, non-binding conformations that disrupt the normal binding-conformation in a G-quartet structure of the original aptamer. The alternate conformations are designed not to bind thrombin. Addition of thrombin to a solution containing the aptamer shifted the equilibrium concentrations of the structures towards the thrombin binding conformation. A fluorescence-quenching pair added to the 5' and 3' ends of some of the bioengineered aptamers allowed determination of the aptamer beacon conformation by observing the fluorescence emission. The equilibrium between different conformations of several possible aptamer beacon candidates was altered by modifying the composition or length of the stem region.

FIGS. 13A-D show one of the newly designed thrombin aptamer beacons. Binding of thrombin (black oval) to the aptamer beacon (FIG. 13A) causes a change in equilibrium between the quenched stem-loop structure (FIG. 13D) to the unquenched conformation (FIG. 13B), going through a straight-chain, unfolded intermediate (FIG. 13C), which shows the full nucleic acid sequence of the new aptamer beacon. The star represents a fluorescent element, e.g., a fluorophore, and the white square represents a quencher element, e.g., a chemical group. The emission intensity of the fluorophore is represented by the size of the star, and increases with the distance between the fluorophore and the quencher. Thus, fluorescence intensity is maximal in FIG. 13C and minimal in FIG. 13D, and about equal in FIGS. 13A and 13B.

The new thrombin aptamer beacons were prepared as follows.

Materials: All the oligonucleotides, including the aptamer beacons, were synthesized using standard DNA synthetic techniques. Aptamer beacons (labeled G15DxxMB) were synthesized by coupling fluorescein at the 5'-end and a DABCYL group at the 3'-end. G15D5dF is G15D5d with 5'-fluorescein, but without any quencher group on the 3'-end. Thrombin and factor IX were purchased from Enzyme Research Lab. Various aptamer beacon candidates were made as follows:

| G15D | GGTTGGTGTGGTTGG | (SEQ ID NO: 1) |
|---|---|---|
| G15D4d | CCAAGGTTGGTGTGGTTGG | (SEQ ID NO: 2) |
| G15D5d | CCAACGGTTGGTGTGGTTGG | (SEQ ID NO: 3) |
| G15D6d | CCAACCGGTTGGTGTGGTTGG | (SEQ ID NO: 4) |
| G15D7d | CCAACCAGGTTGGTGTGGTTGG | (SEQ ID NO: 5) |
| G15D5nd | TTTTTGGTTGGTGTGGTTGG | (SEQ ID NO: 6) |
| G15D5drev | CCAACCACACCAAGTTGG | (SEQ IS NO: 7) |

Competitive binding assay: G15D5d was radiolabeled with [(α-32P] ATP using T4-polynucleotide kinase. Radiolabeled G15D5d (5 nM/5000 cpm) and 0-1 µM of unlabeled aptamers in thrombin binding buffer (TBB) (20 mM Tris-HCl, 140 mM NaCl, 5 mM KCl, 1 mM $MgCl_2$, and 1 mM $CaCl_2$, pH 7.5) were mixed with 10 nM thrombin in 100 µl of TBB. After 15 minutes incubation at room temperature, the solutions were filtered through two layers of filter; nitrocellulose filter (BA85) on the top of a Nylon filter (Hybond-P™) The thrombin-aptamer complexes were collected on nitrocellulose filters, whereas free aptamers were collected on nylon filters. The amount of radio-labeled aptamer on each filter was determined by scintillation counter or by phosphor storage system (BioRad).

Single strand conformation sensitive gel electrophoresis: The single strand conformation sensitive gel electrophoresis was performed on 8% acrylamide gel (75:1 bis:acrylamide ratio) 0.5×TBE (0.045M Tris-borate, 0.002M EDTA pH 8.5) and 10% glycerol in gel. A small volume of radio-labeled aptamers (1 µM) were incubated with or without thrombin (10 µM) in TBB. The samples were mixed with equal volume of 50% glycerol and bromophenol blue (0.05%) and, then loaded on a gel. The electrophoresis was carried out with 300V in a cold room. After the run, the gel was dried and exposed to Kodak X-OMAT film overnight.

Thrombin binding assay using a fluorescence spectrometer: The aptamers were diluted to a concentration of 10 uM in TBB or TE (20 mM Tris-HCl, 1 mM EDTA, pH7.5) and heated at 99° for three min and cooled down to room temperature prior to the experiment. The experiment was performed using 5-40 nM of aptamer in 2 ml. All of the fluorescence intensity measurements were performed at 24° C. The excitation wavelength was 495 nm and the emission was monitored at its peak, 516 nm (in TE) or 518 nm (in TBB). A small volume (0.5-311) of thrombin (final concentration of 0-250 nM) was added and the change of emission was monitored.

Titration with an oligonucleotide containing complement sequence: G15D5dMB at 10 µM was mixed with various concentrations of G15D5drev in TE. The mixtures were heated at 99° for three minutes and then incubated at 50° C. for ten minutes before cooling down to room temperature. The fluorescence intensity was measured at a molecular beacon aptamer concentration of 40 nM.

Figure 14:
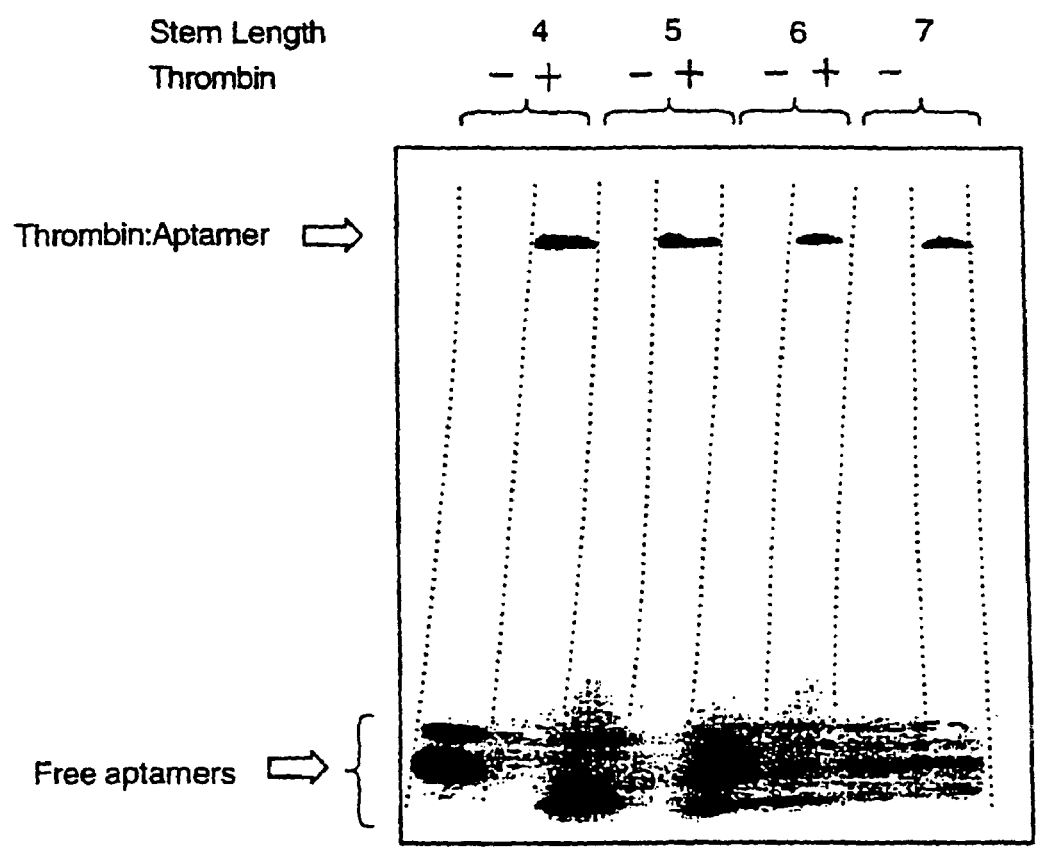
FIG. 14 is a representation of an electrophoresis gel showing various aptamer beacons with and without thrombin.

A preliminary evaluation of the aptamer beacon candidates using the single strand conformation sensitive gel electrophoresis of G15D4d (stem length is 4 nucleotides), G15D5d (stem length is 5), G15D6d (stem length is 6), G15D7d (stem length is 7) revealed that each of these nucleic acids could exist in multiple conformations (FIG. 14; the dashed lines indicate the somewhat curved lanes in the gel). G15D4d existed in 2 conformations in the absence of thrombin, but was fully switched into a single bound conformation upon addition of thrombin. G15D5d existed in 4 conformations in the absence of thrombin, but in a manner similar to G15D4d, was fully switched to a single conformation upon addition of thrombin. G15D6d and G15D7d existed in 4 conformations in the absence of thrombin, but, unlike the other two aptamers, only a fraction of the aptamers could bind with thrombin. These results suggested that G15D4d and G15D5d would make the most likely candidates for creating aptamer beacons. Of these two structures, G15D5d was predicted to be the better candidate because the extra base-pair will stabilize the non-binding structure, resulting in a lower signal in the absence of the target molecule.

FIG. 14 shows free aptamers in the lower half of the gel, and thrombin:aptamer beacon complexes in the top half of the gel. In this figure, + indicates with thrombin, and − indicates without thrombin.

Figure 15:
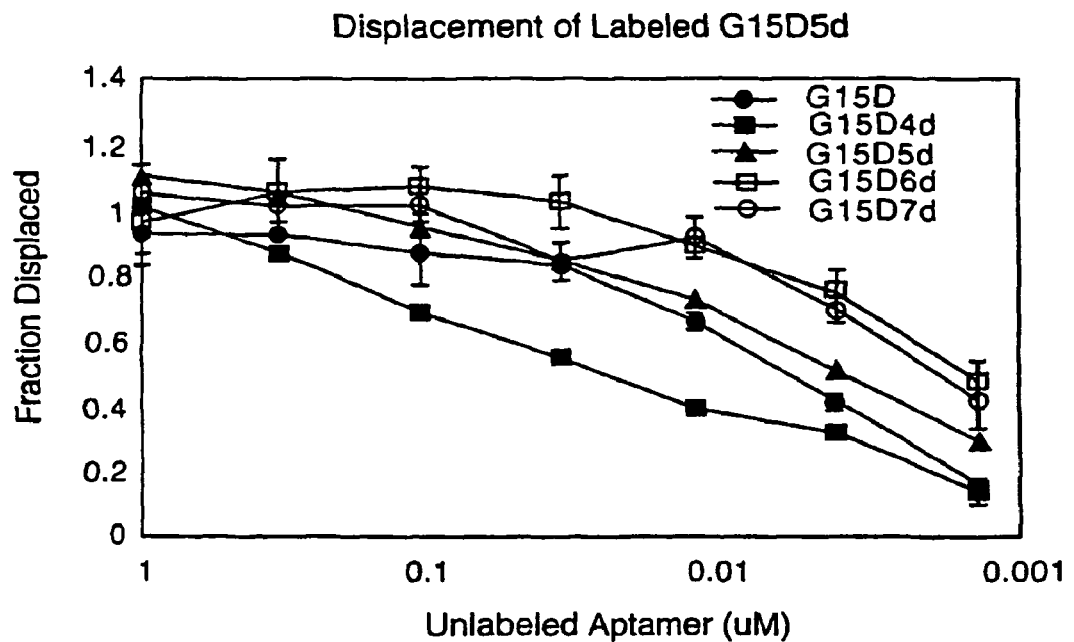
FIG. 15 is a graph showing the displacement of a radiolabeled aptamer beacon (G15D5d) with unlabeled aptamer beacons.

The effect of stem length on thrombin binding was also tested by using a competitive binding assay. The four aptamers with different stem lengths, along with the original G15D aptamer, were tested for binding by a competition assay with radiolabeled G15D5d (FIG. 15). As shown in this graph, G15D4d, 5d and 6d all had similar displacement curves, while G15D7d exhibited decreased binding.

Aptamer beacons G15D4d, G15D5d, and G15D6d, were labeled by adding fluoroscein to the 5'-end and DABCLY group to the 3'-end. These aptamer beacons, G15D4dMB, G15D5dMB and G15D6dMB, were evaluated for their response to varying thrombin concentration (0-120 nM) in either TBB or TE buffers. Table 1 below shows the relative fluorescence intensity of aptamers. The baseline fluorescence intensity of each aptamer beacon was measured at 40 nM aptamer beacon in the absence of thrombin with excitation wavelength at 495 nm (10 nm bandwidth for excitation and emission) using Hitachi fluorescence spectrophotometer F-2500. The average fluorescence intensity changes with the addition of thrombin (100 nM) are shown relative to the baseline intensity of each aptamer beacon. In Table 1, NC indicates no change.

| Aptamer | TBB | TBB + Thrombin | TE | TE + Thrombin |
| --- | --- | --- | --- | --- |
| G15D4dMB | 30 | 1.5 | 98 | NC |
| G15D5dMB | 7.5 | NC | 19 | 2.3 |
| G15D6dMB | 17 | NC | 20 | 1.7 |
| G15D5ndMB | 188 | 0.5 | 1102 | 0.7 |
| G15D5dF | 280 | NC | 380 | NC |

Table 1 shows that G15D5dMB and G15D6dMB were the two best aptamer beacons in TE, and G15D4dMB was best in TBB. When G15D4dMB was able to bind thrombin and increase fluorescence intensity in TBB, G15D5dMB and G15D6dMB failed. However, G15D4dMB did not bind to thrombin in TE, while G15D5dMB and G15D6d MB were capable of interacting with thrombin. The four base-paired duplex as in G15D4dMB may be too unstable in TE, whereas five or six base-paired duplex in G15D5dMB and G15D6dMB may be too stable in TBB to allow the conformational change that is required for thrombin binding. This is consistent with the observation that G15D4dMB has 2-3 fold higher emission than G15D5dMB in TBB, suggesting less duplex conformation. In TE, the baseline of G15D4dMB and G15D5dMB were five to ten-folds higher than those in TBB, suggesting that diminishes the population of the stem-loop structure due to the lack of the divalent cation in the buffer.

Figure 16:
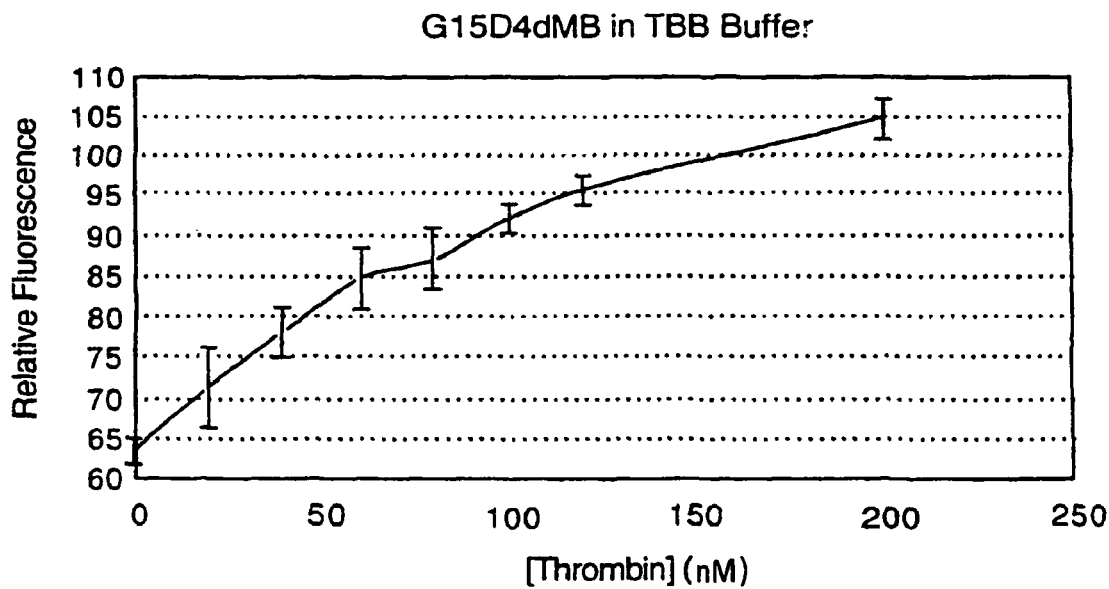
FIG. 16 is a graph showing fluorescence intensity of aptamer beacon G15D4dMB in Thrombin Binding Buffer (TBB) as a function of thrombin concentration.

Next, the change in fluorescence of the aptamer beacons in the Thrombin Binding Buffer was measured. As shown in FIG. 16, G15D4dMB had moderate emission in the absence of thrombin. As thrombin concentration increased, the fluorescence intensity increased, but did not reach saturation within the concentration range (250 nM) tested. This emission change upon the addition of thrombin took approximately 2 minutes to reach its equilibrium value. Both G15D5dMB and G15D6dMB had very low fluorescence emission in the absence of thrombin, and the fluorescence intensity did not change as the thrombin concentration was increased.

Figure 17:
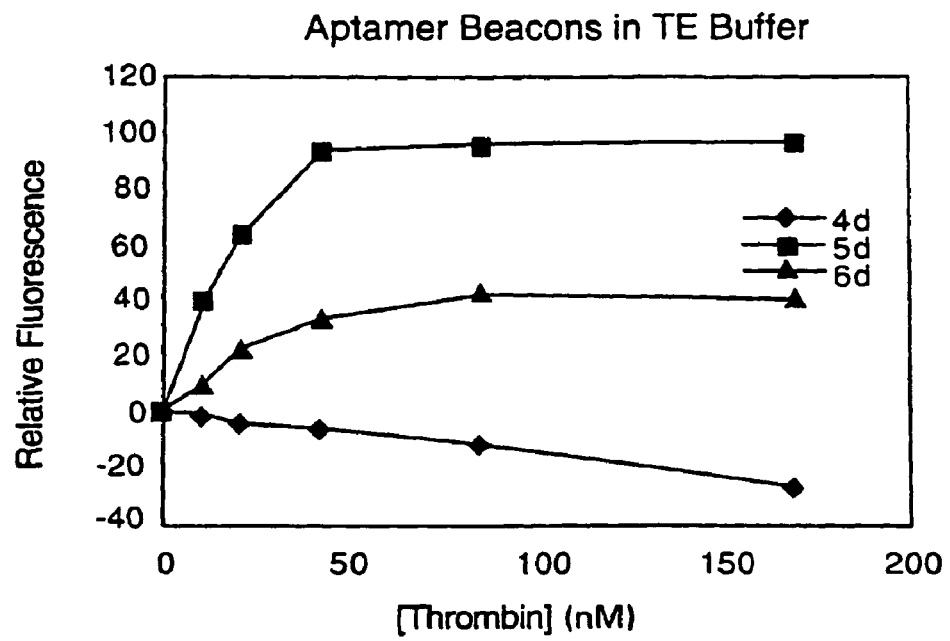
FIG. 17 is a graph showing fluorescence emission of various aptamer beacons in TE buffer as a function of thrombin concentration.

Because the gel electrophoresis measurements (FIG. 14) were performed in a low salt buffer (TBE), we next measured the change in aptamer beacon fluorescence in TE buffer. These results are shown in FIG. 17. In TE buffer, G15D4dMB had much higher emission in the absence of thrombin. (Note that the fluorescence intensity values shown in FIG. 17 are relative to the values listed in Table 1.) The fluorescence emission of G15D4dMB did not increase upon addition of thrombin. G15D5dMB had a relatively low emission in the absence of thrombin that increased with the addition of thrombin. The Kd was estimated to be 3±1 nM. The change in the fluorescence intensity occurred immediately upon addition of thrombin. The fluorescence emission of the G15D6dMB aptamer beacon also increased with the addition of thrombin, but saturated at a lower emission intensity. The estimated Kd (12 nM) was slightly higher than G15D5dMB. The estimated Kd for G15D5dMB is similar to the reported Kd for G15D, which varied from 1.4 nM to 1000 nM. It is possible that the addition of different nucleotides and probes (the fluorophore and the quencher) can attenuate the binding to thrombin. The filter binding competition assay showed approximately 6 fold increase in the affinity for G15D5dMB relative to G15D5d in TE.

Figure 18:
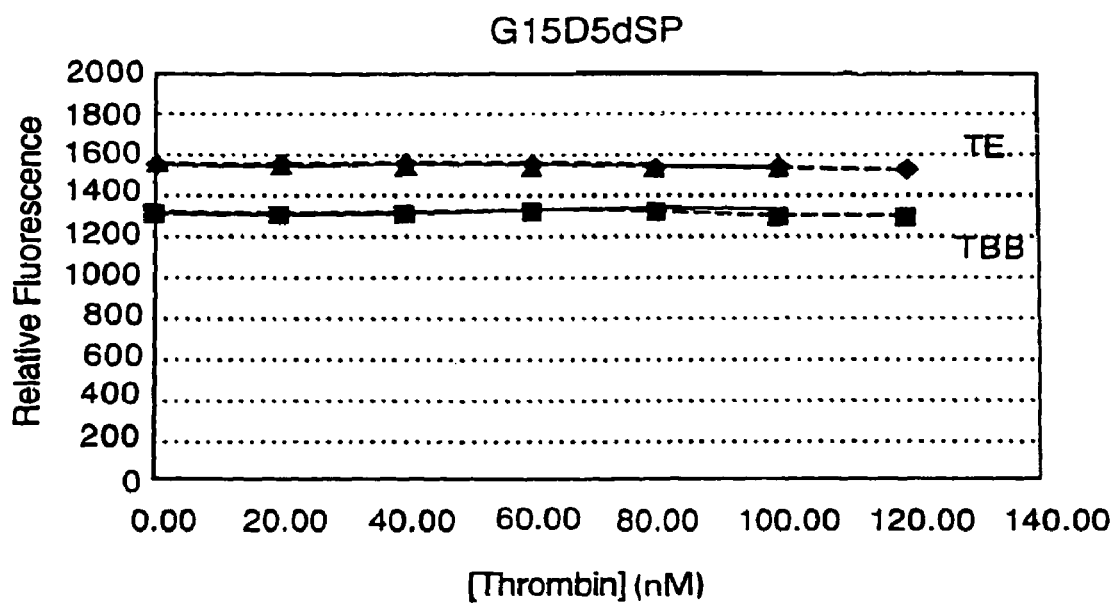
FIG. 18 is a graph showing fluorescence emission of aptamer beacon G15D5dSP as a function of thrombin concentration in TE and TBB buffer.

To eliminate the possibility that the aptamer beacon-thrombin binding is simply causing a change in the chemical environment of the fluorophore, we made an aptamer that had a 5' fluorescein label, but no 3' DABCYL quencher. This aptamer, G15D5dF, showed essentially no change in fluorescence intensity upon addition of thrombin in either TBB or TE buffer (FIG. 18).

Figure 19:
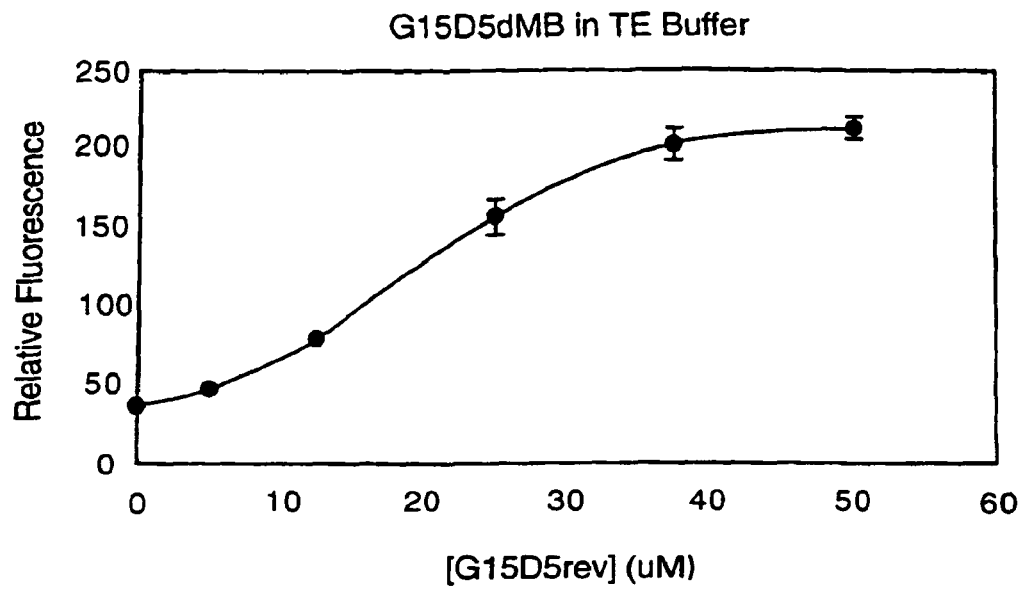
FIG. 19 is a graph showing fluorescence emission of aptamer beacon G15D5dMP in TE buffer as a function of concentration of the complementary oligonucleotide G15D5rev (antisense strand).

The aptamer beacon mechanism should result in a change in fluorescence emission that is similar to the change that would be detected if the same aptamer beacon is used as a standard molecular beacon. To test this hypothesis, we synthesized an oligonucleotide (G15D5rev), which is complementary to G15D5dMB. The concentration-dependent increase in fluorescence intensity of the aptamer beacon when used as a molecular beacon is shown in FIG. 19.

Figure 20:
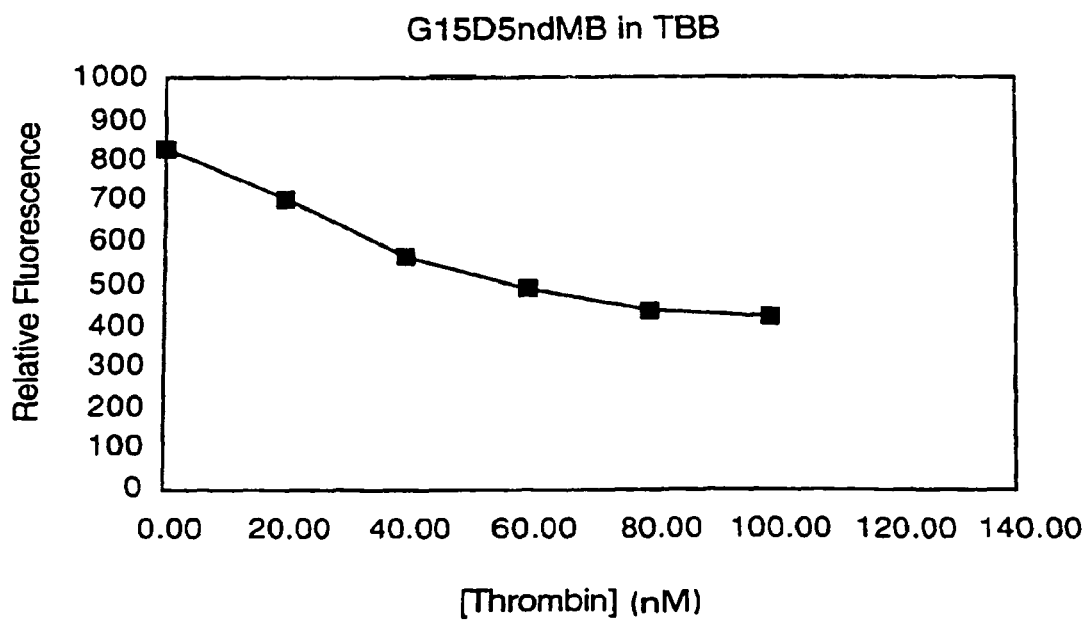
FIG. 20 is a graph showing fluorescence emission of aptamer beacon G15D5ndMB as a function of thrombin concentration in TBB buffer.

As a final demonstration, a modified version of G15D5dMB was made which is no longer able to form the stem loop structure. In this aptamer, G15D5ndMB, the 5' end consists of the sequence TTTTT. Referring to FIGS. 13A-D, addition of thrombin to a solution containing this aptamer should now change the equilibrium between structures A, B, and C, with additional thrombin driving the equilibrium state towards structure A. We first performed this test in TBB to allow stabilization of the thrombin binding conformation. As shown in FIG. 20, addition of thrombin did decrease the fluorescence emission of the aptamer. (Note that because this is a different aptamer, the intensity relative to the original aptamer is not necessarily significant.) The half maximum effect concentration was approximately 80 nM. When we performed this test in TE buffer (data not shown), the fluorescence with no thrombin was approximately 5× that in TBB, and also decreased with the addition of thrombin. Unlike the TBB measurement, it did not saturate within the concentration range tested.

Figure 21:
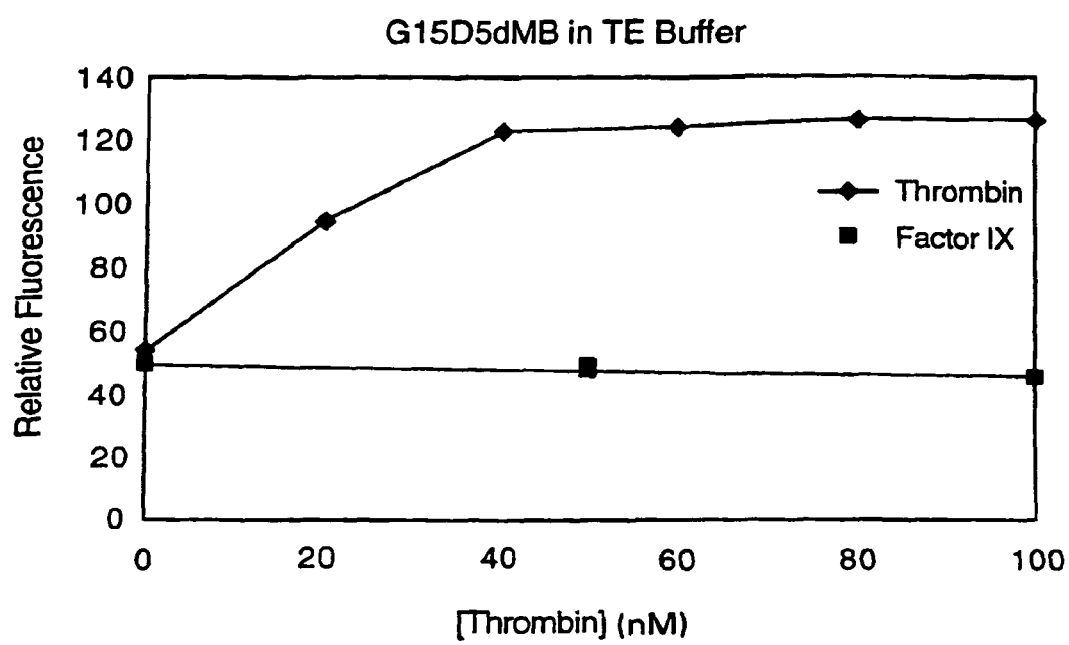
FIG. 21 is a graph showing the effect of thrombin and factor IX on fluorescence of the aptamer beacon G15D5dMB in TE buffer.

To confirm the binding specificity of G15D5dMB, we used factor IX, which is a plasma serine protease, as is thrombin, and shares a sequence identity of 37% in the catalytic domain with thrombin. As shown in FIG. 21, Factor IX, did not affect the fluorescence of G15D5dMB. Although Factor IX is closely related to thrombin, the new aptamer beacons are very specific for thrombin, which shows that the new aptamer beacons do not bind to just any positively charged protein.

Figure 22:
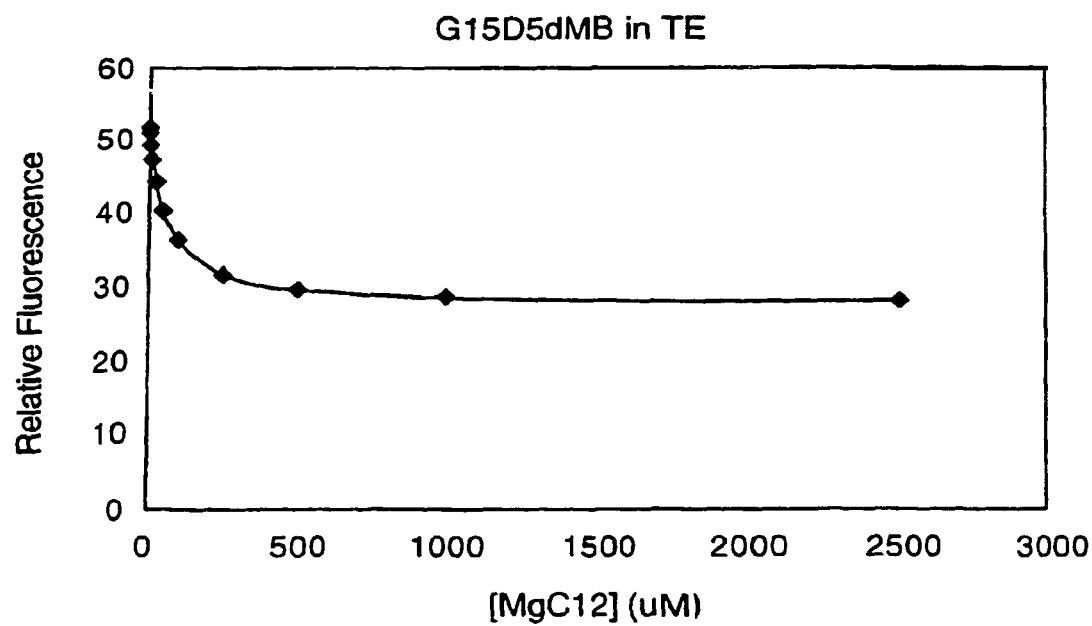
FIG. 22 is a graph showing the effect of magnesium concentration of fluorescence of aptamer beacon G15D5dMB in TE buffer.

Because of the observed differences between aptamer beacon fluorescence in TBB and TE buffer, we examined the effect of cation concentration on the fluorescence of G15D5dMB in the absence of thrombin. The aptamer were prepared as 10 uM in 20 mM Tris-HCl buffer (pH7.5) and the emission of 40 nM G15D5 MB was measured with increasing concentration of MgCl2 (0-2.5 mM). The titration with MgCl2 showed the half maximum effective concentration of 50 uM (FIG. 22). The decreases in the emission by the cations are likely to be due to the stabilization effect on the stem-loop structure. Previously, KCl was reported to decrease the Ki of G15D in thrombin inhibition, but not G15D derivatives. We found that 5 mM of KCl did not have any significant effect in the fluorescence intensity of G15D4dMB. The high concentration of monovalent cation (140 mM NaCl), and 1 mM of divalent cations (Mg++ and Ca++) also lowered the fluorescence.

These results demonstrated that the G15D5dMB was in fact the preferable aptamer beacon, as was determined from the initial single-strand conformation sensitive gel electrophoresis assay of the potential aptamer beacon candidates. These results also demonstrated that the bioengineered aptamer does provide a signal via the aptamer beacon mechanism.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An aptamer beacon that binds to a non-nucleic acid target molecule, the aptamer beacon comprising
    an oligonucleotide comprising a loop portion, a first segment, and a second segment complementary to the first segment, wherein the first and second segments form a stem portion when hybridized together;
    an aptamer binding region formed by the oligonucleotide and configured to bind to the non-nucleic acid target molecule;
    a first reporter moiety attached to the first segment; and
    a second reporter moiety attached to the second segment, wherein the first and second reporter moieties interact to produce a detectable signal when the distance between them is changed;
    wherein binding of the target molecule to the aptamer binding region breaks base pair bonds in the stem portion, causing a change in conformation of the aptamer beacon that separates the first and second segments, thereby altering the distance between the first and second reporter moieties, and produces a detectable signal.

2. The aptamer beacon of claim 1, wherein the first reporter moiety is a fluorophore and the second reporter moiety is a chemical quencher, whereby the quencher quenches the fluorophore when the first and second segments are hybridized together to form the stem portion, and wherein binding of a target molecule to the aptamer binding region breaks base pair bonding in the stem portion, causing the first and second segments to separate and the fluorophore to separate from the chemical group, thereby ending the quenching and enabling the fluorophore to emit detectable fluorescence.

3. The aptamer beacon of claim 1, wherein the aptamer binding region is located within the loop portion, the stem portion, or at least partially in both, within the oligonucleotide.

4. The aptamer beacon of claim 1, wherein the first and second reporter moieties are an enzyme and a corresponding ligand.

5. The aptamer beacon of claim 1, wherein the first and second segments comprise 4, 5, 6, or 7 nucleotides each.

6. The aptamer beacon of claim 1, wherein the target molecule is thrombin.

7. An aptamer beacon that binds to a non-nucleic acid target molecule, the aptamer beacon comprising
    an oligonucleotide comprising a first segment, a second segment, and a third segment located between the first and second segments, wherein the first and second segments form a complex when the aptamer beacon is not bound to the target molecule;
    an aptamer binding region formed by the aptamer beacon when contacting the target molecule;
    a first reporter moiety attached to the first segment; and
    a second reporter moiety attached to the second segment, wherein the first and second reporter moieties interact to produce a detectable signal when the distance between them is changed;
    wherein binding of the target molecule to the aptamer binding region breaks base pair bonds in the complex, causing a change in conformation of the aptamer beacon that alters the distance between the first and second reporter moieties, and produces a detectable signal.

8. The aptamer beacon of claim 7, wherein the first reporter moiety is an energy absorbing moiety and the second reporter moiety is a fluorescence emitting moiety, such that when the first and second reporter moieties are in sufficiently close proximity, the absorbing moiety allows an energy transfer between the moieties, thereby allowing the emitting moiety to emit fluorescence; and wherein binding of a target molecule to the aptamer binding region causes the first and second segments to hybridize together.

9. The aptamer beacon of claim 7, wherein the aptamer binding region is located entirely within the third segment of the oligonucleotide.

10. The aptamer beacon of claim 7, wherein the complex is a duplex.

11. A device for simultaneously detecting the presence of a plurality of different, non-nucleic acid target molecules in a sample, the device comprising:
   a solid support; and
   a plurality of different aptamer beacons bound to the support, each aptamer beacon having a first end attached to the support, and a binding region that binds to a specific non-nucleic acid target molecule, wherein the binding regions of different aptamer beacons bind to different target molecules.

12. The device of claim 11, wherein the solid support comprises a glass surface to which the first ends of the aptamer beacons are covalently bound.

13. The device of claim 11, wherein the solid support comprises a planar surface, and the aptamer beacons are distributed on the planar surface in a two-dimensional array.

14. The device of claim 13, wherein spots of identical aptamer beacons are located at different points in the two-dimensional array.

15. The device of claim 11, wherein the binding region of at least one of the aptamer beacons is configured to bind to a non-nucleic acid target molecule selected from the group consisting of a protein, a steroid, and an inorganic molecule.

16. The device of claim 11, wherein the aptamer beacons comprise RNA, DNA, modified RNA, modified RNA, or a combination thereof.

17. The device of claim 11, wherein each aptamer beacon comprises a reporter group for signaling binding of a target molecule to the binding region.

18. The device of claim 17, wherein the reporter group comprises a fluorophore.

19. A method of detecting the presence or absence of one or more different target molecules in a sample, the method comprising:
   obtaining a plurality of aptamer beacons of claim 1;
   contacting the sample to the aptamer beacons, such that any target molecules in the sample can bind to corresponding binding regions of the aptamer beacons; and
   detecting the presence of target molecules bound to the aptamer beacons.

20. The method of claim 19, wherein the aptamer beacons are in a liquid.

21. The method of claim 19, wherein the aptamer beacons are bound to a solid support.

22. The method of claim 19, wherein the solid support is a particle.

23. The method of claim 19, wherein the solid support is a plate.

24. The method of claim 19, wherein the aptamer beacons emit fluorescent radiation when excited by evanescent waves.

25. The method of claim 23, wherein different spots, each spot comprising a plurality of identical aptamer beacons, are distributed on the solid support in a predetermined array, and the method further comprises comparing a fluorescence pattern of the sample to known fluorescence patterns.

26. The method of claim 25, wherein the comparing step includes the use of a computer program, disposed on a computer readable medium, the computer program including instructions for causing a processor to:
   compare the fluorescence pattern of the sample to a library of known fluorescence patterns; and
   select the combination of known fluorescence patterns that most closely matches the fluorescence pattern of the sample.

27. The method of claim 19, wherein the detecting step includes detecting a change in the Raman emission frequencies of an aptamer beacon, the change caused by binding of a target molecule to the aptamer beacon.

28. The method of claim 23, wherein the solid support comprises a metal film to which the aptamers are bound, and the detecting step includes detecting a change in the resonant condition of surface plasmons in the metal film caused by binding of a target molecule to an aptamer beacon.

29. A device for detecting the presence of a target molecule in a sample, the device comprising:
   a solid support; and
   a plurality of different aptamer beacons bound to the support, each aptamer beacon having a first end attached to the support, and a binding region that binds to a specific enantiomer of the target molecule or a specific binding site of the target molecule, wherein the binding regions of different aptamer beacons bind to different enantiomers of the target molecule or to different binding sites of the target molecule.

30. The device of claim 29, wherein the target comprises an antigen, and the different binding sites comprise different epitopes of the antigen.

31. The device of claim 29, wherein the target comprises a bacteria, and the different binding sites comprise different surface proteins of the bacteria.

32. A system for simultaneously detecting the presence of a plurality of different non-nucleic acid target molecules in a sample, the system comprising:
   a plurality of different aptamer beacons of claim 1, each aptamer beacon having a first end attached to the support, a binding region that binds to a specific non-nucleic acid target molecule, the binding regions of different aptamers binding to different target molecules; and
   a detection system that detects the presence of target molecules bound to aptamer beacons, the detection system comprising a radiation source and a detector.

33. The system of claim 32, wherein the radiation source comprises a laser.

34. The system of claim 32, further comprising an analyzer to determine the presence of target molecules in the sample based on the output of the detector, wherein the analyzer comprises a computer processor programmed to:
   compare the output of the detector to a library of known outputs corresponding to exposing samples of known composition to the aptamer beacons; and
   select a combination of known outputs that most closely matches the assay outputs.

35. The system of claim 32, wherein the aptamer beacons are in a liquid.

36. The system of claim 32, wherein the aptamer beacons are attached to a solid support.

37. The aptamer beacon of claim 1, wherein the oligonucleotide comprises RNA or modified RNA.

38. The aptamer beacon of claim 1, wherein the oligonucleotide comprises DNA or modified DNA.

39. A system for simultaneously detecting the presence of a plurality of different non-nucleic acid target molecules in a sample, the system comprising:
   a plurality of different species of aptamer beacons of claim 1, wherein each species of aptamer beacons has a different reporter group, a binding region that binds to a specific non-nucleic acid target molecule, and wherein the binding regions of different aptamers bind to different target molecules; and
   a detection system that detects the presence of target molecules bound to aptamer beacons, the detection system being able to detect the different reporter groups.

* * * * *